(12) United States Patent
Takashima et al.

(10) Patent No.: US 11,631,242 B2
(45) Date of Patent: Apr. 18, 2023

(54) INFORMATION PROCESSING APPARATUS, INFORMATION PROCESSING METHOD, AND PROGRAM

(71) Applicant: Sony Group Corporation, Tokyo (JP)

(72) Inventors: Masatoshi Takashima, Tokyo (JP); Hideki Date, Kanagawa (JP); Yu Kitamura, Kanagawa (JP)

(73) Assignee: Sony Group Corporation, Tokyo (JP)

( * ) Notice: Subject to any disclaimer, the term of this patent is extended or adjusted under 35 U.S.C. 154(b) by 199 days.

(21) Appl. No.: 17/257,702

(22) PCT Filed: Jul. 2, 2019

(86) PCT No.: PCT/JP2019/026237
§ 371 (c)(1),
(2) Date: Jan. 4, 2021

(87) PCT Pub. No.: WO2020/013024
PCT Pub. Date: Jan. 16, 2020

(65) Prior Publication Data
US 2021/0295042 A1    Sep. 23, 2021

(30) Foreign Application Priority Data

Jul. 10, 2018 (JP) .............................. JP2018-130474

(51) Int. Cl.
*G06V 20/10* (2022.01)
*G06V 10/143* (2022.01)

(52) U.S. Cl.
CPC .......... *G06V 20/188* (2022.01); *G06V 10/143* (2022.01)

(58) Field of Classification Search
CPC   G06T 7/0012; G01B 11/303; G01N 33/2823; G01N 21/359; G01D 5/35345;
(Continued)

(56) References Cited

U.S. PATENT DOCUMENTS

2017/0339340 A1* 11/2017 De Bayser .......... G10L 15/1822
2019/0051502 A1*  2/2019 Asakura ............ H01J 37/32926

FOREIGN PATENT DOCUMENTS

| CN | 103528965 A | 1/2014 |
| CN | 107578412 A | 1/2018 |

(Continued)

OTHER PUBLICATIONS

International Search Report (PCT/ISA/210), International Application No. PCT/JP2019/026237, dated Oct. 14, 2019.

(Continued)

*Primary Examiner* — Phuoc H Doan
(74) *Attorney, Agent, or Firm* — Michael Best & Friedrich LLP

(57) ABSTRACT

Selection of an evaluation index based upon statistical values of respective evaluation indices is disclosed. In one example, an information processing apparatus comprises an evaluation index unit that determines a plurality of evaluation indices on a basis of imaging data obtained by imaging a subject, wherein the evaluation indices are respectively based upon different wavelength component combinations of the imaging data. An evaluation value unit determines an evaluation value based on a statistical value of each of the evaluation indices, for each of the evaluation indices. A selection unit then determines a selected evaluation index from the evaluation indices on a basis of the evaluation values.

26 Claims, 27 Drawing Sheets

(58) Field of Classification Search
CPC ........ G01K 11/32; G01H 9/004; G01H 13/00;
G02F 1/35; G06K 9/2018; G01M 5/0041
USPC .................................................. 382/110, 131
See application file for complete search history.

(56) References Cited

FOREIGN PATENT DOCUMENTS

| | | |
|---|---|---|
| JP | 2003339238 A | 12/2003 |
| JP | 2005025503 A | 1/2005 |
| JP | 2006250827 A | 9/2006 |
| JP | 2006314215 A | 11/2006 |
| WO | 2017/10258 A1 | 1/2017 |

OTHER PUBLICATIONS

Written Opinion of the International Search Authority (PCT/ISA/237), International Application No. PCT/JP2019/026237, dated Oct. 14, 2019.
Genevieve Rondeaux , Optimization of Soil-Adjusted Vegetation Indices , Remote Sensing of Environment , Feb. 2, 1996 , vol. 55, No. 2 , 95-107.
Yves M. Govaerts , Designing optimal spectral indices: A feasibility and proof of concept study , International Journal of Remote Sensing , vol. 20 No. 9 , Jun. 15, 1999 , 1853-1873.

* cited by examiner

FIG. 13
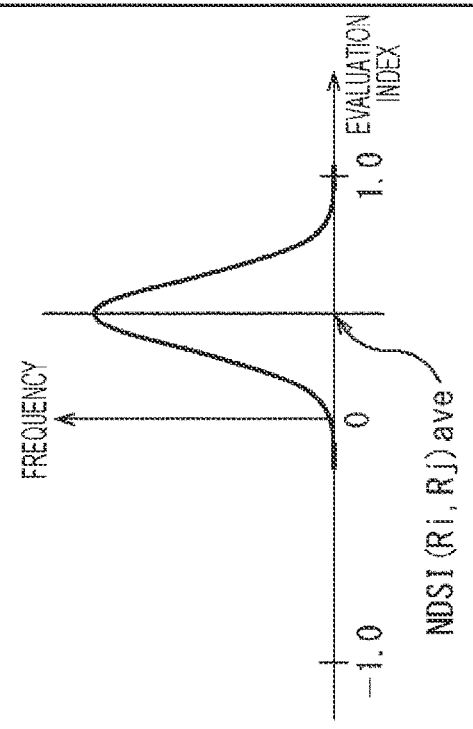
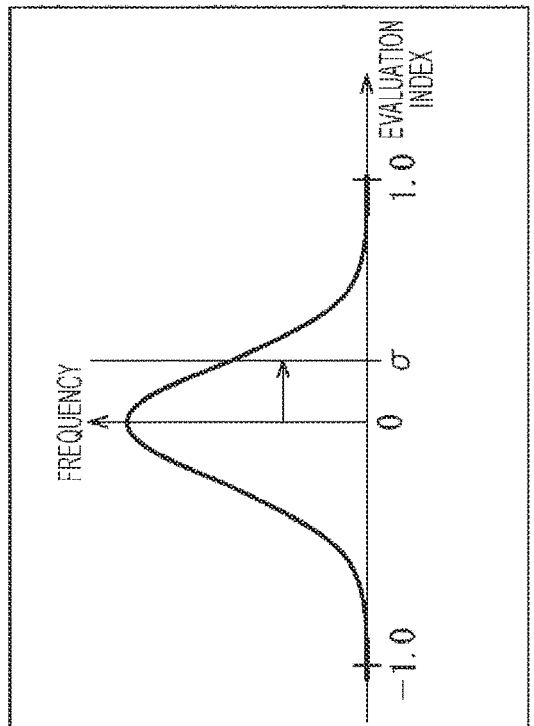

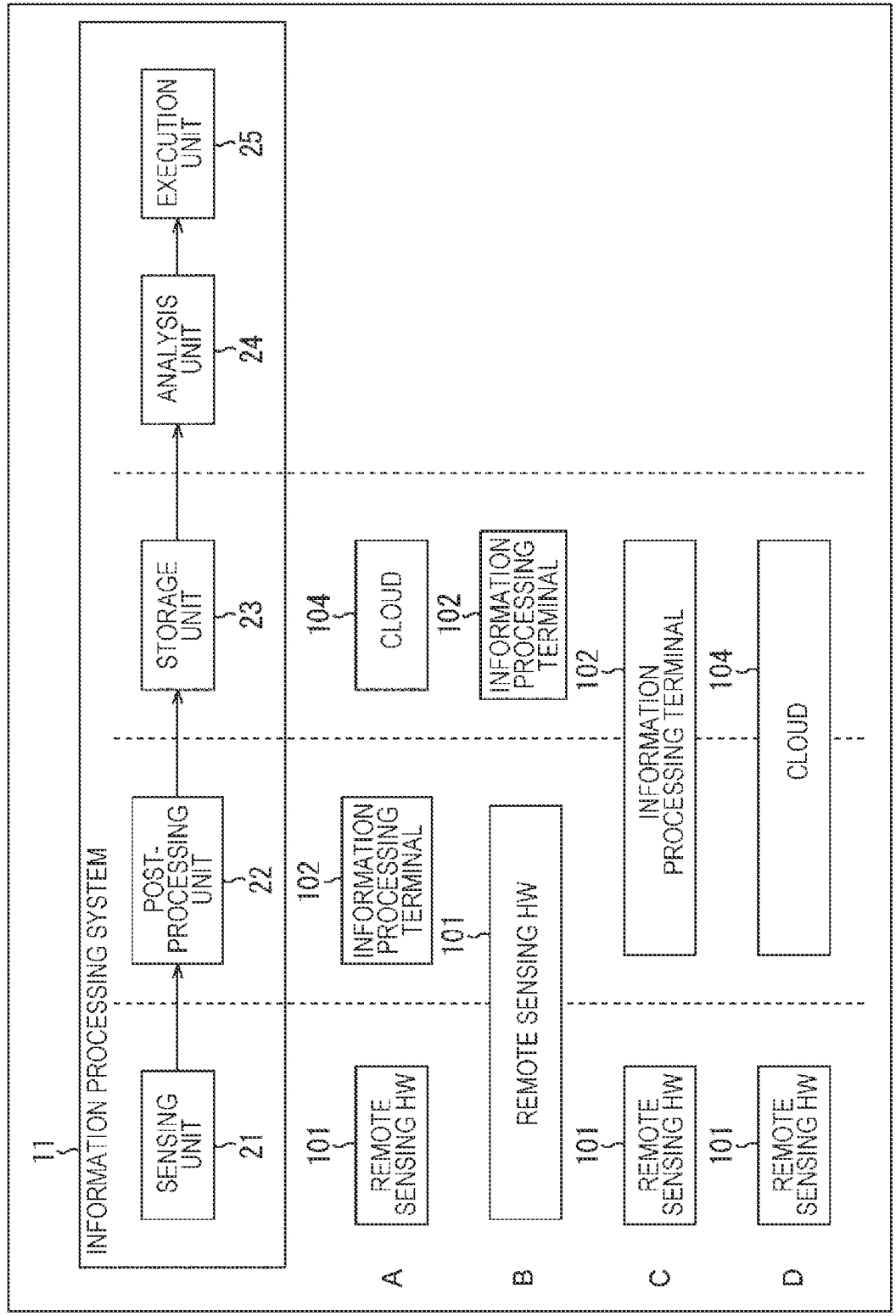

INFORMATION PROCESSING APPARATUS, INFORMATION PROCESSING METHOD, AND PROGRAM

TECHNICAL FIELD

The present technology relates to an information processing apparatus, an information processing method, and a program and in particular, to an information processing apparatus, an information processing method, and a program suitable for use in analyzing a subject in an image using an evaluation index.

CROSS REFERENCE TO RELATED APPLICATIONS

This application claims the benefit of Japanese Priority Patent Application JP 2018-130474 filed on Jul. 10, 2018, the entire contents of which are incorporated herein by reference.

BACKGROUND ART

An evaluation index based on multiple wavelength components, such as a normalized difference vegetation index (NDVI), is used for analysis of a subject in a captured image, for example, for analysis of vegetation, soil, or the like of the agricultural land for agricultural use (for example, refer to PTL 1).

CITATION LIST

Patent Literature

PTL 1: WO 2017/10258 A

SUMMARY OF INVENTION

Technical Problem

Even for the same subject, the same evaluation index is not necessarily appropriate depending on the state or the like. For example, in the case of the NDVI that is an evaluation index calculated on the basis of two wavelength components of red light and near-infrared light in an image, when the growth of agricultural crops exceeds a certain level, changes in these two wavelength components in the image are reduced. Accordingly, since it is difficult to sufficiently grasp a change in the state of the agricultural land with the NDVI, there is a possibility that the accuracy of analysis will be lowered.

It is desirable to make it possible to use an appropriate evaluation index for analysis of a subject.

Solution to Problem

An information processing apparatus according to an aspect of the present technology includes: an evaluation index calculation unit that calculates a plurality of types of evaluation indices on the basis of imaging data obtained by imaging a subject; an evaluation value calculation unit that calculates an evaluation value based on a statistical value of each of the evaluation indices for each of the evaluation indices; and a selection unit that selects the evaluation index on the basis of the evaluation value.

An information processing method according to an aspect of the present technology includes: calculating a plurality of types of evaluation indices on the basis of imaging data obtained by imaging a subject by an information processing apparatus; calculating an evaluation value based on a statistical value of each of the evaluation indices for each of the evaluation indices by the information processing apparatus; and selecting the evaluation index on the basis of the evaluation value by the information processing apparatus.

A program according to an aspect of the present technology causes a computer to execute processes of: calculating a plurality of types of evaluation indices on the basis of imaging data obtained by imaging a subject; calculating an evaluation value based on a statistical value of each of the evaluation indices for each of the evaluation indices; and selecting the evaluation index on the basis of the evaluation value.

According to the aspect of the present technology, a plurality of types of evaluation indices are calculated on the basis of imaging data obtained by imaging the subject, an evaluation value based on the statistical value of each of the evaluation indices is calculated for each of the evaluation indices, and the evaluation index is selected on the basis of the evaluation value.

Advantageous Effects of Invention

According to the embodiment of the present technology, it is possible to use an appropriate evaluation index for analysis of a subject.

In addition, the effects described herein are not necessarily limited, and may be any of the effects described in the present technology.

BRIEF DESCRIPTION OF DRAWINGS

FIG. 13 is a diagram for explaining evaluation index normalization processing.

FIG. 28 is a block diagram showing a modification example of the configuration of an information processing system.

DESCRIPTION OF EMBODIMENTS

Hereinafter, embodiments for carrying out the present technology will be described. The description will be given in the following order.

1. First embodiment
2. Second embodiment
3. Modification example
4. Others

1. First Embodiment

First, a first embodiment of the present technology will be described with reference to FIGS. 1 to 22.

<Configuration Example of Information Processing System 11>

Figure 1:
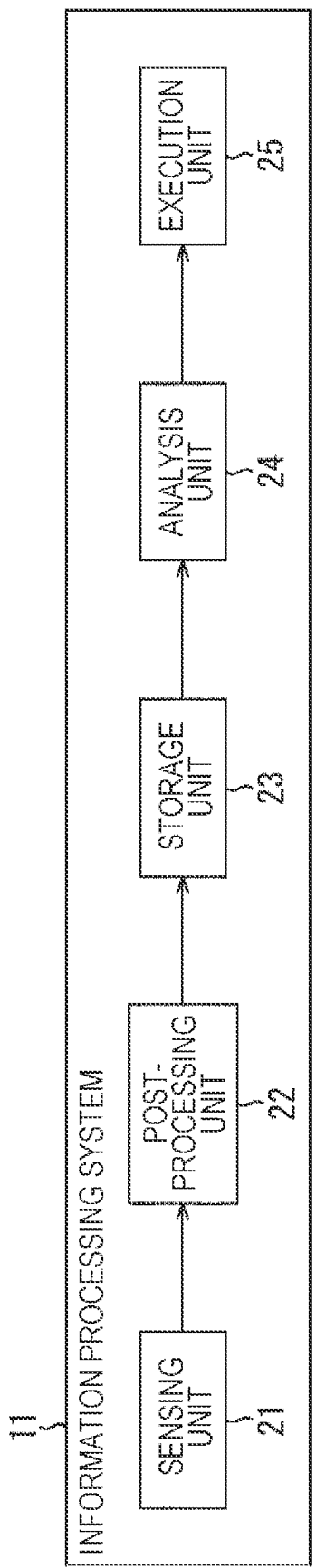
FIG. 1 is a block diagram showing a first embodiment of an information processing system to which the present technology is applied.

FIG. 1 shows a configuration example of a function of an information processing system 11 to which the present technology is applied.

The information processing system 11 is, for example, a system that senses a region to be analyzed (hereinafter, referred to as a sensing area), such as an agricultural land, analyzes a sensing result, and performs various actions on the basis of the analysis result. The information processing system 11 includes a sensing unit 21, a post-processing unit 22, a storage unit 23, an analysis unit 24, and an execution unit 25.

The sensing unit 21 senses the sensing area. For example, the sensing unit 21 images the sensing area, or the like, and supplies sensing data including data of the obtained captured image (hereinafter, referred to as a sensing image) to the post-processing unit 22.

In addition, hereinafter, the data of the sensing image is also simply referred to as a sensing image.

The post-processing unit 22 calculates an evaluation index used for analysis of a subject (for example, a sensing area) in the sensing image on the basis of the sensing image. The post-processing unit 22 stores data indicating the calculation result of the evaluation index (hereinafter, referred to as evaluation index data) in the storage unit 23.

The analysis unit 24 performs various analyses on the sensing area on the basis of the evaluation index data stored in the storage unit 23, and supplies data indicating the analysis result (hereinafter, referred to as analysis data) to the execution unit 25.

The execution unit 25 executes various actions on the basis of the analysis data.

Figure 2:
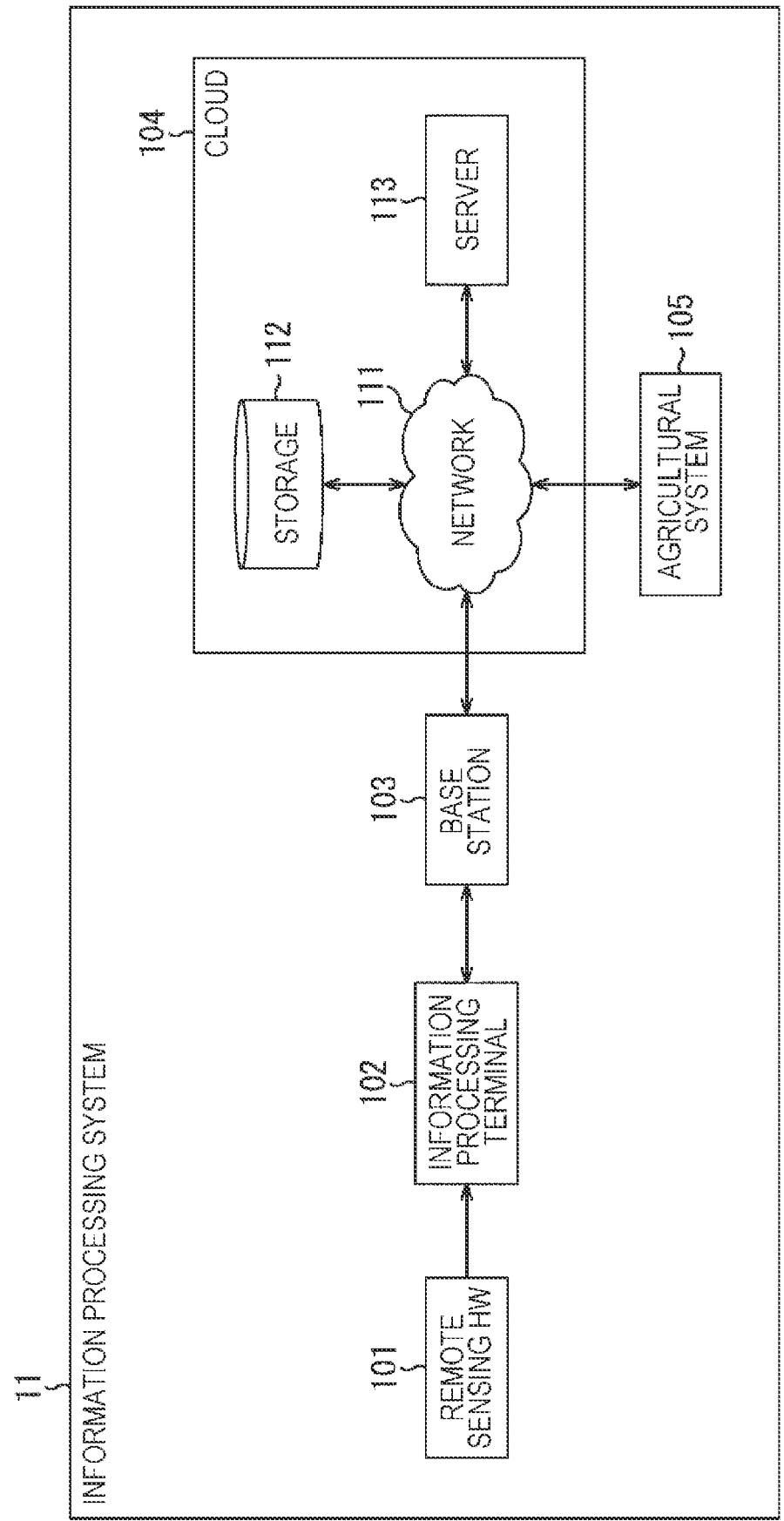
FIG. 2 is a block diagram showing a specific configuration example of the information processing system shown in FIG. 1.

FIG. 2 shows a specific configuration example for realizing the information processing system 11 in FIG. 1. In addition, portions corresponding to those in FIG. 1 are denoted by the same reference numerals.

The information processing system 11 shown in FIG. 2 includes a remote sensing HW 101, an information processing terminal 102, a base station 103, a cloud computing (hereinafter, simply referred to as a cloud) 104, and an agricultural system 105.

The remote sensing HW 101 has a function of the sensing unit 21 shown in FIG. 1. The remote sensing HW 101 senses the sensing area, and supplies the obtained sensing data to the information processing terminal 102.

The information processing terminal 102 is, for example, a mobile device, such as a personal computer (PC) or a smartphone, and has a function of the post-processing unit 22 shown in FIG. 1. The information processing terminal 102 calculates an evaluation index used for analysis of the sensing area on the basis of the sensing data. In addition, the information processing terminal 102 performs wired communication or wireless communication with the base station 103 according to a predetermined communication method, and transmits evaluation index data indicating the calculation result of the evaluation index and the like to the base station 103.

The base station 103 connects the information processing terminal 102 to a network 111, and performs relay of data between the information processing terminal 102 and the network 111 and the like.

The cloud 104 includes the network 111, a storage 112, and a server 113, and realizes the storage unit 23 and the analysis unit 24 shown in FIG. 1. The base station 103, the storage 112, and the server 113 are connected to each other through the network 111.

The network 111 is, for example, a communication network such as the Internet. In addition, the network 111 may include a plurality of communication networks.

The storage 112 has a function of the storage unit 23 shown in FIG. 1. The storage 112 stores the evaluation index data transmitted from the information processing terminal 102, the analysis data transmitted from the server 113, and the like.

The server 113 has a function of the analysis unit 24 shown in FIG. 1. The server 113 analyzes the sensing area on the basis of the evaluation index data stored in the storage 112. If necessary, the server 113 stores the analysis data indicating the analysis result in the storage 112 or transmits the analysis data indicating the analysis result to the agricultural system 105 through the network 111. In addition, for example, the server 113 generates control data for controlling the operation of the agricultural system 105 on the basis of the analysis result, and transmits the control data f to the agricultural system 105 through the network 111.

The agricultural system 105 includes various agricultural machines, such as a tractor and a sprinkler, and has a function of the execution unit 25 shown in FIG. 1. For example, the agricultural system 105 performs various actions, such as fertilization and sprinkling, on agricultural crops and the like in the sensing area on the basis of the analysis data or the control data. For example, the agricultural system 105 adjusts the amount of fertilization or the amount of sprinkling according to the growth situation or the like of agricultural crops in the sensing area.

In addition, the number of constituent elements (remote sensing HW 101 or the like) forming the information processing system 11 can be two or more.

<Configuration Example of Remote Sensing HW 101>

Next, a configuration example of the remote sensing HW 101 will be described with reference to FIGS. 3 to 5.

Figure 3:
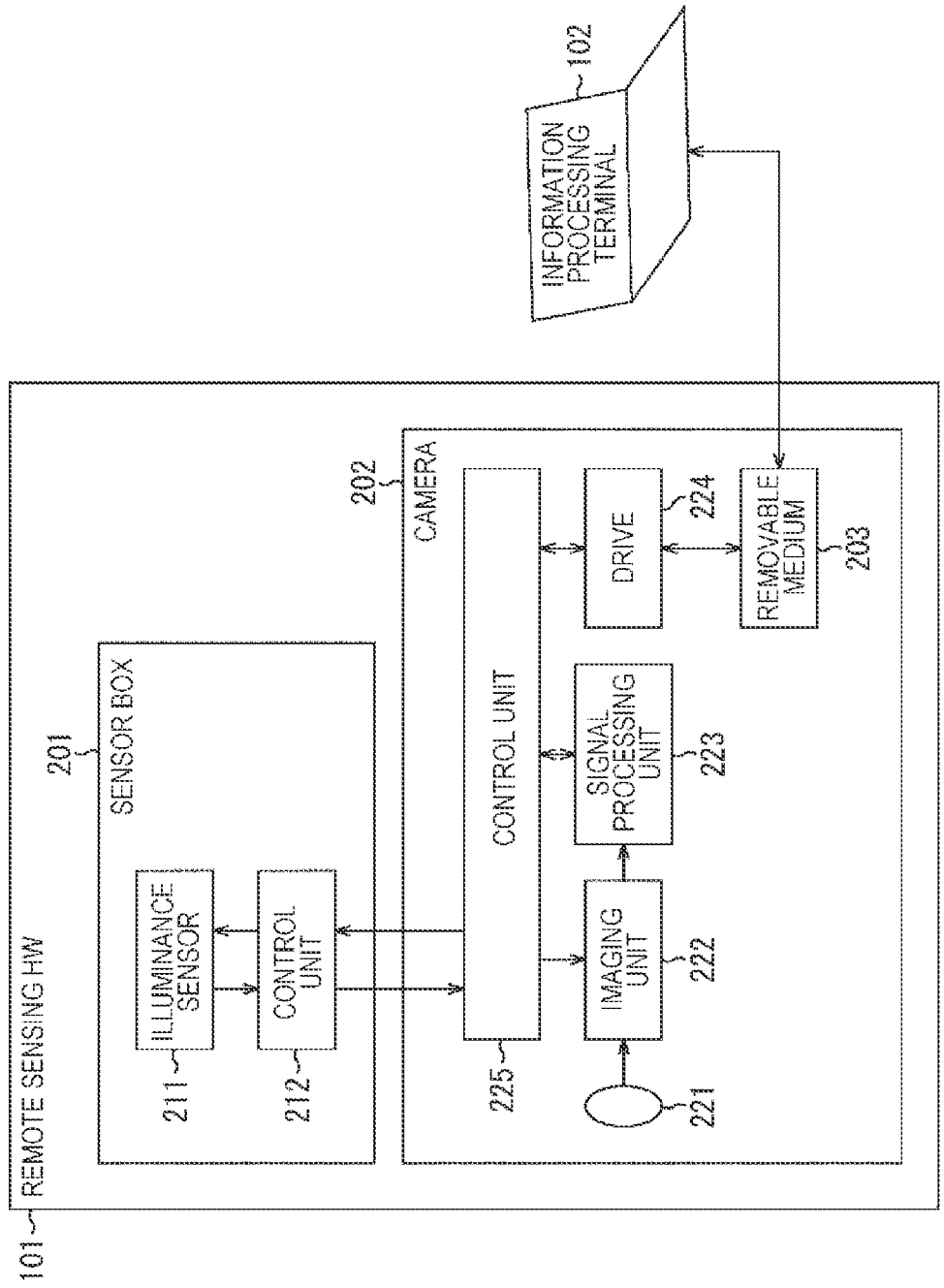
FIG. 3 is a block diagram showing a configuration example of a remote sensing HW.

FIG. 3 is a block diagram showing a configuration example of the remote sensing HW 101. The remote sensing HW 101 includes a sensor box 201 and a camera 202.

The sensor box 201 includes an illuminance sensor 211 and a control unit 212.

The illuminance sensor 211 detects the illuminance of a plurality of predetermined wavelength bands (for example, red, blue, green, infrared light, and the like) of ambient light, such as sunlight, under the control of the control unit 212, for example. In this manner, the rough spectral characteristics of a light source (for example, sun) of ambient light are detected. The illuminance sensor 211 supplies data indicating the detection result (hereinafter, referred to as light source data) to the control unit 212.

The control unit 212 controls the detection timing and the like of the illuminance sensor 211 in cooperation with a control unit 225 of the camera 202. In addition, the control unit 212 supplies the light source data to the control unit 225 of the camera 202.

The camera 202 includes an optical system 221, an imaging unit 222, a signal processing unit 223, a drive 224, and the control unit 225.

The optical system 221 includes a lens and the like, and forms an image of a subject on the light receiving surface of an image sensor 242 (FIG. 4) of the imaging unit 222.

Under the control of the control unit 225, the imaging unit 222 images a subject (sensing area), and supplies the obtained sensing image to the signal processing unit 223.

Under the control of the control unit 225, the signal processing unit 223 performs various kinds of signal processing on the sensing image, and supplies the sensing image after signal processing to the control unit 225.

The drive 224 drives a removable medium 203 under the control of the control unit 225. For example, the drive 224 stores the sensing data including the sensing image and the light source data in the removable medium 203.

The removable medium 203 is, for example, a storage medium that can be detachably mounted on the drive 224, such as a magnetic disk, an optical disc, a magneto-optical disc, or a semiconductor memory.

The control unit 225 performs control of each unit (for example, exposure control of the imaging unit 222, or the like) of the camera 202. In addition, the control unit 225 performs control of synchronization with the sensor box 201 and the like.

<Configuration Example of Imaging Unit 222>

Figure 4:
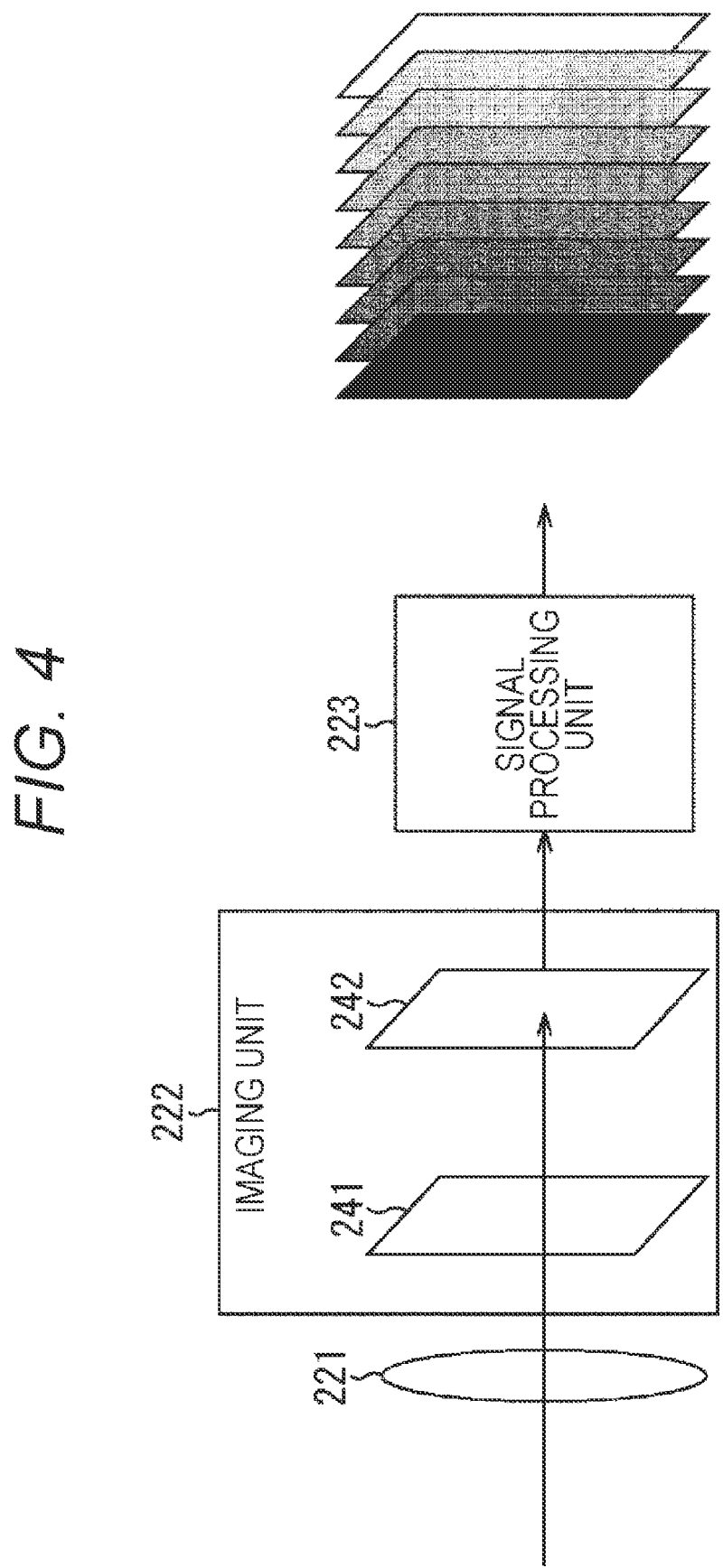
FIG. 4 is a block diagram showing a configuration example of an imaging unit.

FIG. 4 shows a configuration example of the imaging unit 222 of the camera 202. The imaging unit 222 includes a filter 241 and the image sensor 242.

The filter 241 is, for example, a multi-spectral filter or a hyperspectral filter capable of transmitting light beams having wavelengths of two or more predetermined narrow wavelength bands (narrow bands). In this case, the camera 202 is a multi-spectral camera or a hyperspectral camera. In addition, specific examples of such a filter include a plasmon filter, a Fabry-Perot interferometer, and the like.

In addition, the number of wavelength bands (hereinafter, referred to as transmission bands) that the filter 241 transmits can be set to an arbitrary number of two or more. In addition, the range of each transmission band of the filter 241 can also be arbitrarily set.

In addition, the filter 241 can also be known RGB (red, green, and blue) and CMYG (cyan, magenta, yellow, and green) color filters and the like.

The image sensor 242 is, for example, a CMOS image sensor or a CCD image sensor. The image sensor 242 captures a sensing image including the components of the transmission band of the filter 241, and supplies the captured sensing image to the signal processing unit 223.

The signal processing unit 223 performs various kinds of signal processing on the sensing image. For example, the signal processing unit 223 performs demosaic processing on the sensing image to perform interpolation processing on components of each transmission band of the filter 241 for each pixel of the sensing image. As a result, each pixel of the sensing image includes components of each transmission band of the filter 241, and the sensing image becomes an image obtained by superimposing a plurality of images for each transmission band of the filter 241. The signal processing unit 223 supplies the sensing image after signal processing to the control unit 225.

<Installation Example of Remote Sensing HW 101>

Figure 5:
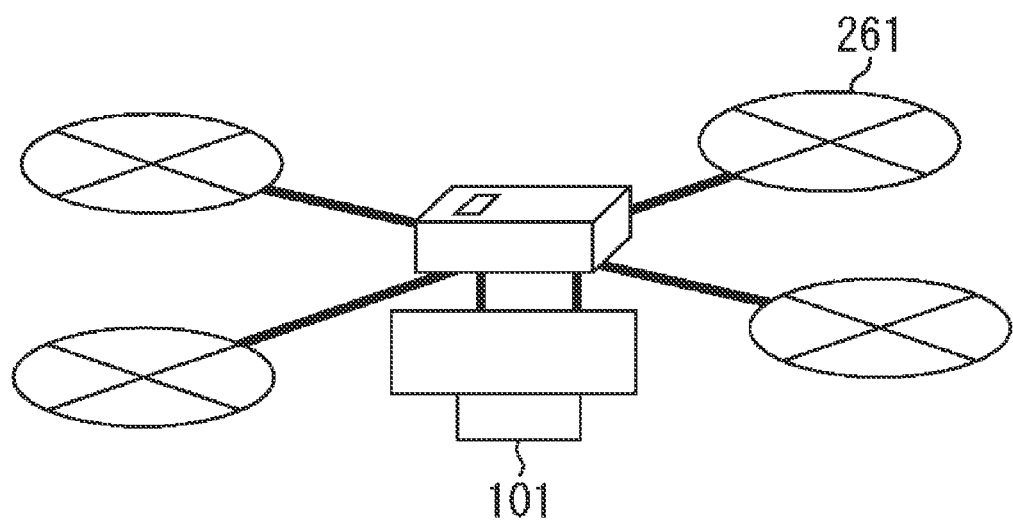
FIG. 5 is a diagram showing an installation example of the remote sensing HW.

FIG. 5 shows an installation example of the remote sensing HW 101.

The remote sensing HW 101 is installed on the lower surface of the main body of a drone 261, for example. Then, the remote sensing HW 101 performs remote imaging (remote sensing) of the sensing area while looking down on the sensing area from the sky.

<Configuration Example of Information Processing Terminal 102>

Figure 6:
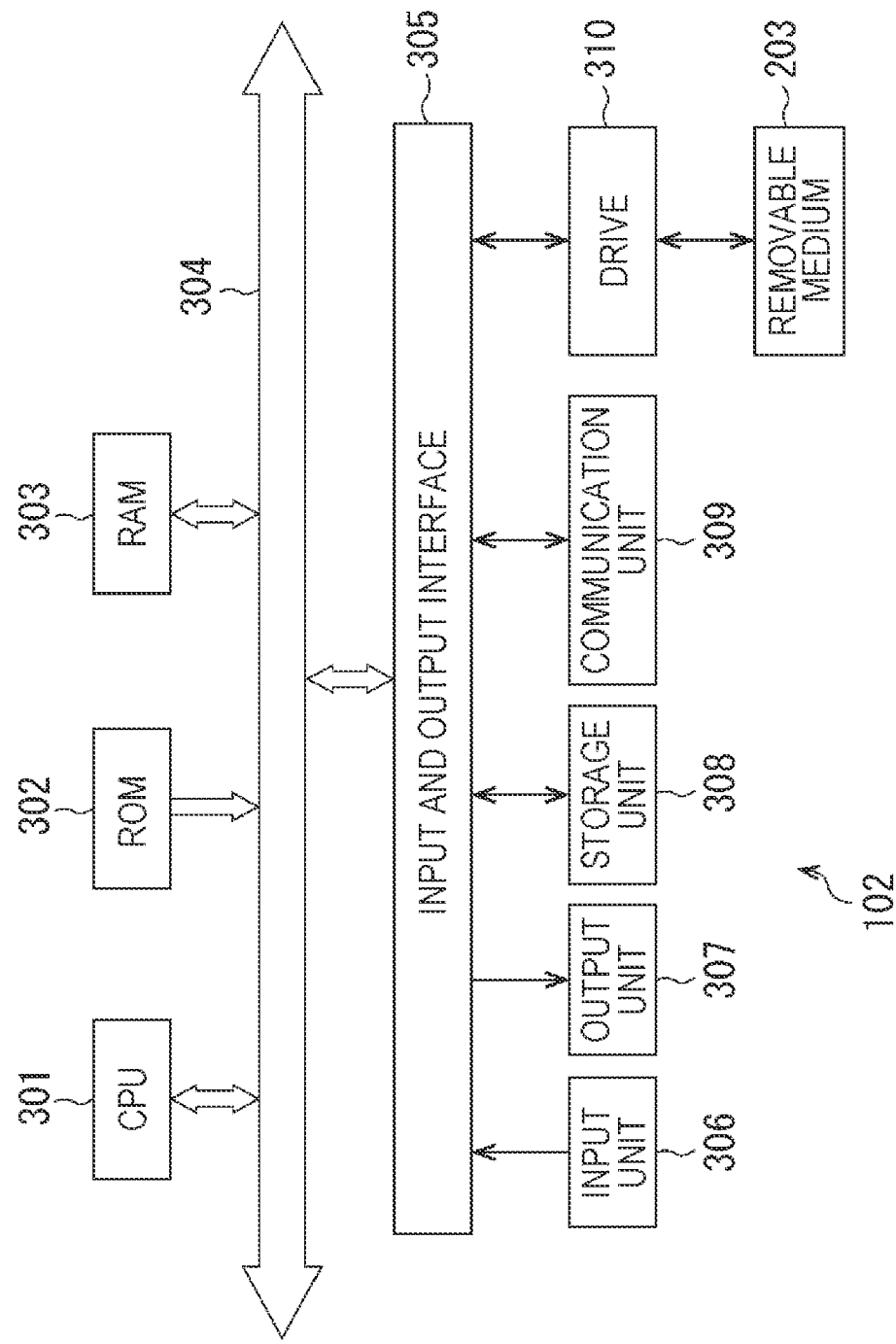
FIG. 6 is a block diagram showing a configuration example of an information processing terminal.

FIG. 6 shows a configuration example in a case where the information processing terminal 102 is a PC.

In the information processing terminal 102, a central processing unit (CPU) 301, a read only memory (ROM) 302, and a random access memory (RAM) 303 are connected to each other by a bus 304.

An input and output interface 305 is further connected to the bus 304. An input unit 306, an output unit 307, a storage unit 308, a communication unit 309, and a drive 310 are connected to the input and output interface 305.

The input unit 306 includes an input switch, a button, a microphone, an imaging element, and the like.

The output unit 307 includes a display, a speaker, and the like.

The storage unit 308 includes a hard disk, a nonvolatile memory, and the like.

The communication unit 309 includes a network interface, a communication device, and the like.

The drive 310 drives the removable medium 203. For example, the drive 310 reads sensing data written by the remote sensing HW 101 from the removable medium 203.

In addition, descriptions of the bus 304 and the input and output interface 305 will be omitted hereinafter in the case of describing the information processing terminal 102. For example, in a case where the CPU 301 transmits and receives data to and from the communication unit 309 through the bus 304 and the input and output interface 305, this is simply stated that the CPU 301 transmits and receives data to and from the communication unit 309.

<Configuration Example of Information Processing Unit 331>

Figure 7:
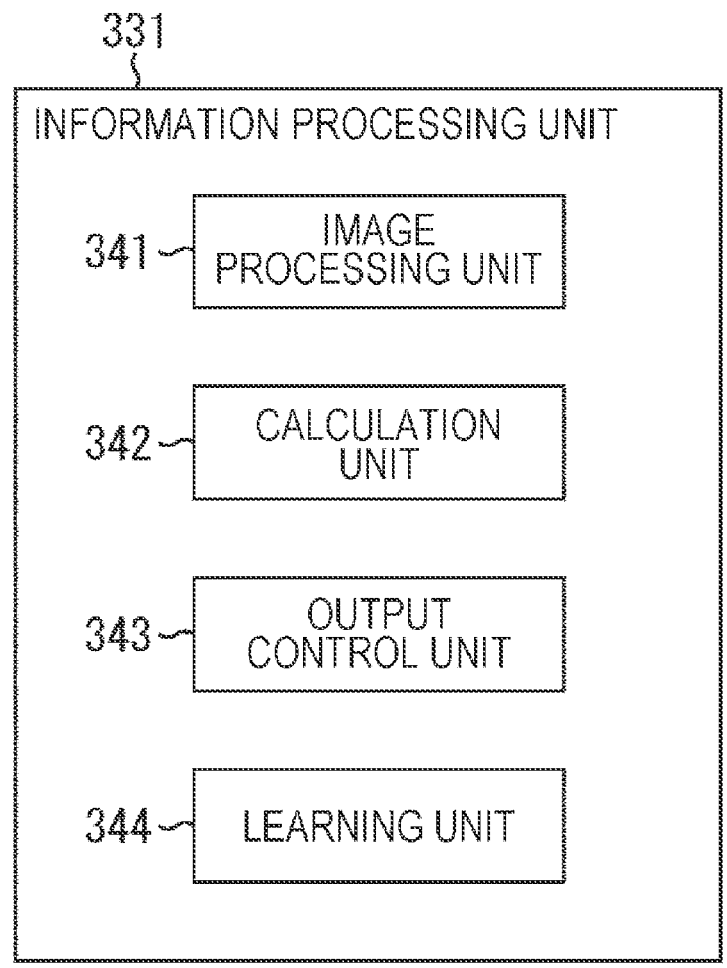
FIG. 7 is a block diagram showing a first embodiment of an information processing unit.

FIG. 7 shows a configuration example of the information processing unit 331 realized by executing a predetermined control program by the CPU 301 of the information processing terminal 102.

The information processing unit 331 includes an image processing unit 341, a calculation unit 342, an output control unit 343, and a learning unit 344.

The image processing unit 341 performs various kinds of image processing on the sensing image and the evaluation index data. For example, the image processing unit 341 performs stitch processing and the like on the sensing image and the evaluation index data.

The calculation unit 342 calculates an evaluation index on the basis of the sensing data and generates evaluation index data indicating the calculation result of the evaluation index.

The output control unit 343 controls output of an image, sound, and the like from the output unit 307.

The learning unit 344 learns selection conditions for selecting the evaluation index.

<Configuration Example of Calculation Unit 342>

Figure 8:
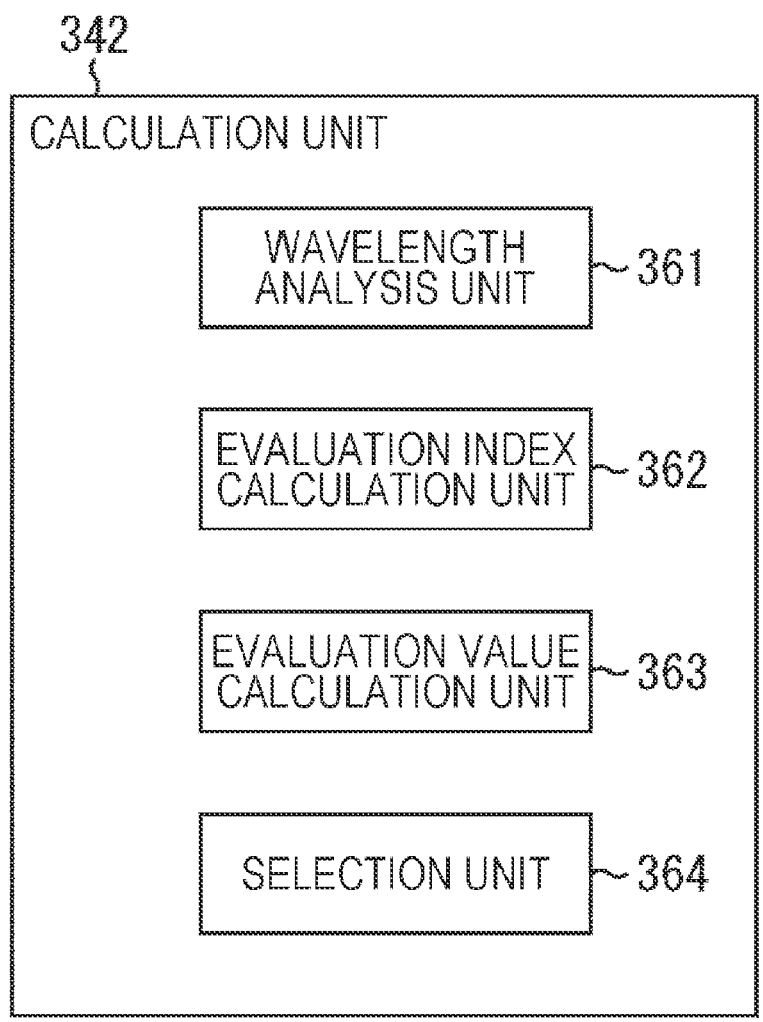
FIG. 8 is a block diagram showing a configuration example of a calculation unit.

FIG. 8 shows a configuration example of the calculation unit 342 of the information processing unit 331 shown in FIG. 7.

The calculation unit 342 includes a wavelength analysis unit 361, an evaluation index calculation unit 362, an evaluation value calculation unit 363, and a selection unit 364.

The wavelength analysis unit 361 detects the spectral characteristics of the sensing image on the basis of the sensing data. More specifically, the wavelength analysis unit 361 detects the spectral characteristics of the reflectance of the subject (for example, the sensing area) in the sensing image (hereinafter, simply referred to as the spectral characteristics of the subject). As a result, a plurality of wavelength components are extracted from the sensing image.

The evaluation index calculation unit 362 calculates a plurality of types of evaluation indices for the same sensing image on the basis of the spectral characteristics of the sensing image, more specifically, the spectral characteristics of the subject. In addition, the evaluation index calculation unit 362 generates evaluation index data based on each evaluation index.

The evaluation value calculation unit 363 calculates an evaluation value for each evaluation index on the basis of a statistical value for each of the plurality of types of evaluation indices.

The selection unit 364 selects an evaluation index used for analysis of the sensing area on the basis of the evaluation value for each evaluation index or the given selection conditions.

First Embodiment of Evaluation Index Calculation Processing

Next, a first embodiment of evaluation index calculation processing executed by the information processing terminal 102 will be described with reference to the flowchart shown in FIG. 9.

In step S1, the information processing terminal 102 acquires sensing data. For example, the removable medium 203 storing the sensing data is mounted on the drive 310 of the information processing terminal 102. The sensing data includes a sensing image obtained by imaging the sensing area by the remote sensing HW 101 and light source data detected at the time of imaging. The drive 310 reads the sensing data from the removable medium 203, and supplies the read sensing data to the CPU 301.

In step S2, the wavelength analysis unit 361 performs wavelength analysis. That is, the wavelength analysis unit 361 detects the spectral characteristics of the subject (sensing area) in the sensing image to detect the reflectance for each predetermined wavelength of the subject.

Here, an example of a method of detecting the spectral characteristics of a subject will be described with reference to FIGS. 10A and 10B.

FIGS. 10A and 10B show examples of the spectral characteristics $L(\lambda)$ of a light source of ambient light, such as sunlight, the spectral characteristics $P(\lambda)$ of a subject, the spectral characteristics $S(\lambda)$ of an imaging system (imaging unit 222 in FIG. 4), and the spectral characteristics $O(\lambda)$ of a sensing image. FIG. 10A shows an example of spectral characteristics in a case where the filter 241 shown in FIG. 4 is a Fabry-Perot interferometer. FIG. 10B shows an example of spectral characteristics in a case where the filter 241 shown in FIG. 4 is a plasmon filter.

The spectral characteristics $O(\lambda)$ of the sensing image are obtained by multiplying the spectral characteristics $L(\lambda)$ of the light source, and the spectral characteristics $P(\lambda)$ of the subject, and the spectral characteristics $S(\lambda)$ of the imaging system. That is, the spectral characteristics $O(\lambda)$ of the sensing image are expressed by the following Equation (1).

$$O(\lambda)=L(\lambda) \times P(\lambda) \times S(\lambda) \tag{1}$$

Here, the spectral characteristics $L(\lambda)$ of the light source can be calculated on the basis of the light source data included in the sensing data. The spectral characteristics $S(\lambda)$ of the imaging system is known from the design values of the filter 241 and the image sensor 242 of the imaging unit 222 and the like. Therefore, the wavelength analysis unit 361 calculates the spectral characteristics $P(\lambda)$ of the subject by performing a predetermined calculation on the basis of the spectral characteristics $L(\lambda)$ of the light source, the spectral characteristics $S(\lambda)$ of the imaging system, and the spectral characteristics $O(\lambda)$ of the sensing image.

For example, the wavelength analysis unit 361 detects a component of a set wavelength of each pixel of the sensing image while shifting the wavelength at a predetermined interval (for example, every 1 mm) within a predetermined wavelength range. As a result, the spectral characteristics of the sensing image are detected. Then, the wavelength analysis unit 361 calculates the spectral characteristics of the subject by performing an inverse matrix calculation of the spectral characteristics of the light source and the spectral characteristics of the imaging system with respect to the detected spectral characteristics of the sensing image. As a result, the reflectance of the subject with respect to light of each wavelength is detected for each pixel of the sensing image.

The wavelength analysis unit 361 supplies data indicating the detection result of the spectral characteristics of the subject to the evaluation index calculation unit 362.

In step S3, the information processing terminal 102 executes evaluation index selection processing, and then the process proceeds to step S4.

Here, the details of the evaluation index selection processing will be described with reference to the flowchart shown in FIG. 11.

In step S31, the evaluation index calculation unit 362 selects a combination of wavelengths. Specifically, the evaluation index calculation unit 362 selects one combination for which an evaluation index has not yet been calculated, among the combinations of two different wavelengths among wavelengths for which the reflectance of the subject has been detected (hereinafter, referred to as detection target wavelengths).

In step S32, the evaluation index calculation unit 362 calculates an evaluation index based on the selected wavelength. For example, the evaluation index calculation unit 362 calculates a normalized difference spectral index (NDSI) as an evaluation index for each pixel of the sensing image using the following Equation (2).

$$NDSI(Ri,Rj)=(Rj-Ri)/(Rj+Ri)=(1-Ri/Rj)/(1+Ri/Rj) \quad (2)$$

In addition, Ri indicates the reflectance of the subject with respect to light having a wavelength $\lambda i$, and Rj indicates the reflectance of the subject with respect to light having a wavelength $\lambda j$. The wavelength $\lambda i$ and the wavelength $\lambda j$ indicate the wavelengths selected in the processing of step S3.

Thus, the evaluation index (NDSI) is calculated on the basis of the components of the wavelength $\lambda i$ and the wavelength $\lambda j$ of the sensing image (more specifically, the reflectance of the subject in the sensing image with respect to light having the wavelength $\lambda i$ and the wavelength $\lambda j$).

In addition, the evaluation index calculation unit 362 generates evaluation index data in which the evaluation indices of the respective pixels of the sensing image are arranged in the arrangement order of the pixels. Therefore, the evaluation index data is data of an image in which the evaluation index of each pixel is a pixel value. The evaluation index calculation unit 362 supplies the generated evaluation index data to the evaluation value calculation unit 363, and stores the generated evaluation index data in the storage unit 308.

In step S33, the evaluation value calculation unit 363 executes evaluation value calculation processing, and then the process proceeds to step S34.

Here, the details of the evaluation value calculation processing will be described with reference to the flowchart shown in FIG. 12.

In step S61, the evaluation value calculation unit 363 sets a target area. The target area is a region in the sensing image as a calculation target of the evaluation value. For example, the target area may be set by the user, or may be automatically set by the evaluation value calculation unit 363. In addition, for example, it is also possible to set all regions of the sensing image as target areas.

In step S62, the evaluation value calculation unit 363 calculates an average value of the evaluation index in the target area. For example, the evaluation value calculation unit 363 calculates the average value of the evaluation index in the target area by integrating the evaluation index of each pixel in the target area and dividing the integrated value by the number of pixels in the target area.

In step S63, the evaluation value calculation unit 363 normalizes the evaluation index. For example, by repeating the processing of the following steps 1 to 4, the evaluation value calculation unit 363 normalizes the evaluation index so that an average value NDSI(Ri, Rj)ave of the evaluation index in the target area becomes 0 (operation point of the evaluation index is 0).

(Step 1)

The evaluation value calculation unit 363 calculates (Ri/Rj)ave by the following Equation (3).

$$(Ri/Rj)\text{ave}=(1-NDSI(Ri,Rj)\text{ave})/(1+NDSI(Ri,Rj)\text{ave}) \quad (3)$$

(Step 2)

The evaluation value calculation unit 363 recalculates the evaluation index of each pixel in the target area using the following Equations (4) and (5).

$$K=X0/(Ri/Rj)\text{ave} \quad (4)$$

$$NDSI(Ri,Rj)=(1-K*(Ri/Rj))/(1+K*(Ri/Rj)) \quad (5)$$

In addition, X0 is the value of Ri/Rj in a case where the evaluation index is 0, and is 1.

(Step 3)

The evaluation value calculation unit 363 recalculates the average value NDSI(Ri, Rj)ave of the evaluation index on the basis of the evaluation index NDSI(Ri, Rj) after recalculation of each pixel in the target area.

(Step 4)

In a case where the average value NDSI(Ri, Rj)ave of the evaluation index deviates from 0, the evaluation value calculation unit 363 returns to step 1, and performs the processing from step 1. On the other hand, in a case where the average value NDSI(Ri, Rj)ave is equal to 0, the evaluation value calculation unit 363 ends the normalization processing.

FIGS. 13A and 13B show an example of a histogram of the evaluation index in the target area before normalization and after normalization, that is, a distribution of the value of the evaluation index of each pixel in the target area before normalization and after normalization. The horizontal axis of FIGS. 13A and 13B indicates an evaluation index. The vertical axis of FIGS. 13A and 13B indicates a frequency, that is, the number of pixels having evaluation index values on the horizontal axis in the target area. In addition, in FIGS. 13A and 13B, an example of a case where the evaluation index having the maximum frequency of the histogram matches the average value NDSI(Ri, Rj)ave of the evaluation index in the target area is shown.

FIG. 13A shows an example of a histogram of the evaluation index before normalization. In this example, the average value NDSI(Ri, Rj)ave of the evaluation index is a value deviated from 0.

FIG. 13B shows an example of a histogram of the evaluation index after normalization. The average value NDSI(Ri, Rj)ave of the evaluation index is normalized to 0 by repeating the processing of steps 1 to 4 described above.

In step S64, the evaluation value calculation unit 363 calculates an evaluation value on the basis of the standard deviation of the evaluation index. Specifically, on the basis of the evaluation index after normalization, the evaluation value calculation unit 363 calculates a standard deviation a of the evaluation index in the target area using the following Equation (6).

$$\sigma = \sqrt{\frac{1}{n}\sum_{i=1}^{n}(NDSI\, i - NDSlave)^2} \quad (6)$$

In addition, NDSIi in Equation (6) indicates an evaluation index after normalization of the i-th pixel in the target area, and n indicates the number of pixels in the target area.

α on the horizontal axis in FIG. 13B indicates an example of the standard deviation of the evaluation index calculated by this processing.

Then, the evaluation value calculation unit 363 sets the calculated standard deviation a as an evaluation value for the evaluation index based on the current wavelength combination.

This evaluation value indicates the scattering degree of the evaluation index in the target area. Therefore, as the evaluation value for the evaluation index becomes larger, for example, the range in which information regarding the sensing area (more precisely, a region in the sensing area corresponding to the target area in the sensing image) can be expressed becomes wider. For example, with an evaluation index having a larger evaluation value, a difference or change in state in the sensing area can be expressed in more detail.

Thereafter, the evaluation value calculation processing is ended.

Returning to FIG. 11, in step S34, the evaluation index calculation unit 362 determines whether or not the calculation has been performed for all the wavelength combinations. In a case where there is a remaining combination for which an evaluation index has not yet been calculated among the combinations of two different wavelengths among the detection target wavelengths, the evaluation index calculation unit 362 determines that the calculation has not yet been performed for all the wavelength combinations, and the process returns to step S31.

Thereafter, the processing of steps S31 to S34 is repeatedly executed until it is determined that the calculation has been performed for all the wavelength combinations in step S34.

As a result, for all combinations of two wavelengths among the detection target wavelengths, an evaluation index and an evaluation value for the evaluation index are calculated for each combination of wavelengths. That is, an evaluation index is calculated for each combination of two wavelength components of the sensing image, and evaluation values for the plurality of calculated evaluation indices are calculated.

On the other hand, in step S34, in a case where there is no remaining combination for which an evaluation index has not been calculated among the combinations of two wavelengths among the detection target wavelengths, the evaluation index calculation unit 362 determines that the calculation has been performed for all the wavelength combinations, and the process proceeds to step S35.

In step S35, the evaluation index calculation unit 362 selects an evaluation index to be used. Specifically, the evaluation value calculation unit 363 supplies data indicating the calculation result of the evaluation value of each evaluation index to the selection unit 364.

The selection unit 364 selects an evaluation index having the maximum evaluation value (that is, the standard deviation a of the evaluation index) as an evaluation index to be used for analysis of the sensing area. As a result, a combination of wavelengths to be used for the evaluation index to be used for analysis of the sensing area is selected. The selection unit 364 supplies data indicating the selection result of the evaluation index to the evaluation index calculation unit 362, and stores the data in the storage unit 308.

In addition, a plurality of types of evaluation indices may be selected. In addition, for example, a plurality of types of selected evaluation index candidates may be presented to the user for the user's selection.

Thereafter, the evaluation index selection processing is ended.

Returning to FIG. 9, in step S4, the information processing terminal 102 outputs evaluation index data based on the selected evaluation index. Specifically, the evaluation index calculation unit 362 reads evaluation index data based on the evaluation index selected by the selection unit 364, among the evaluation index data based on evaluation indices having different wavelength combinations, from the storage unit 308. Then, for example, the evaluation index calculation unit 362 transmits the read evaluation index data to the storage 112 through the communication unit 309, the base station 103, and the network 111, so that the read evaluation index data is stored in the storage 112. In addition, for example, the evaluation index calculation unit 362 deletes all the pieces of evaluation index data from the storage unit 308 as necessary.

Thereafter, the evaluation index calculation processing is ended.

As described above, an evaluation index suitable for the analysis of the sensing area, in other words, a highly effective evaluation index is selected. For example, an evaluation index indicating the state, change, and the like of the sensing area more appropriately is selected. As a result, the analysis accuracy of the state, change, and the like of the sensing area is improved.

Figure 14:
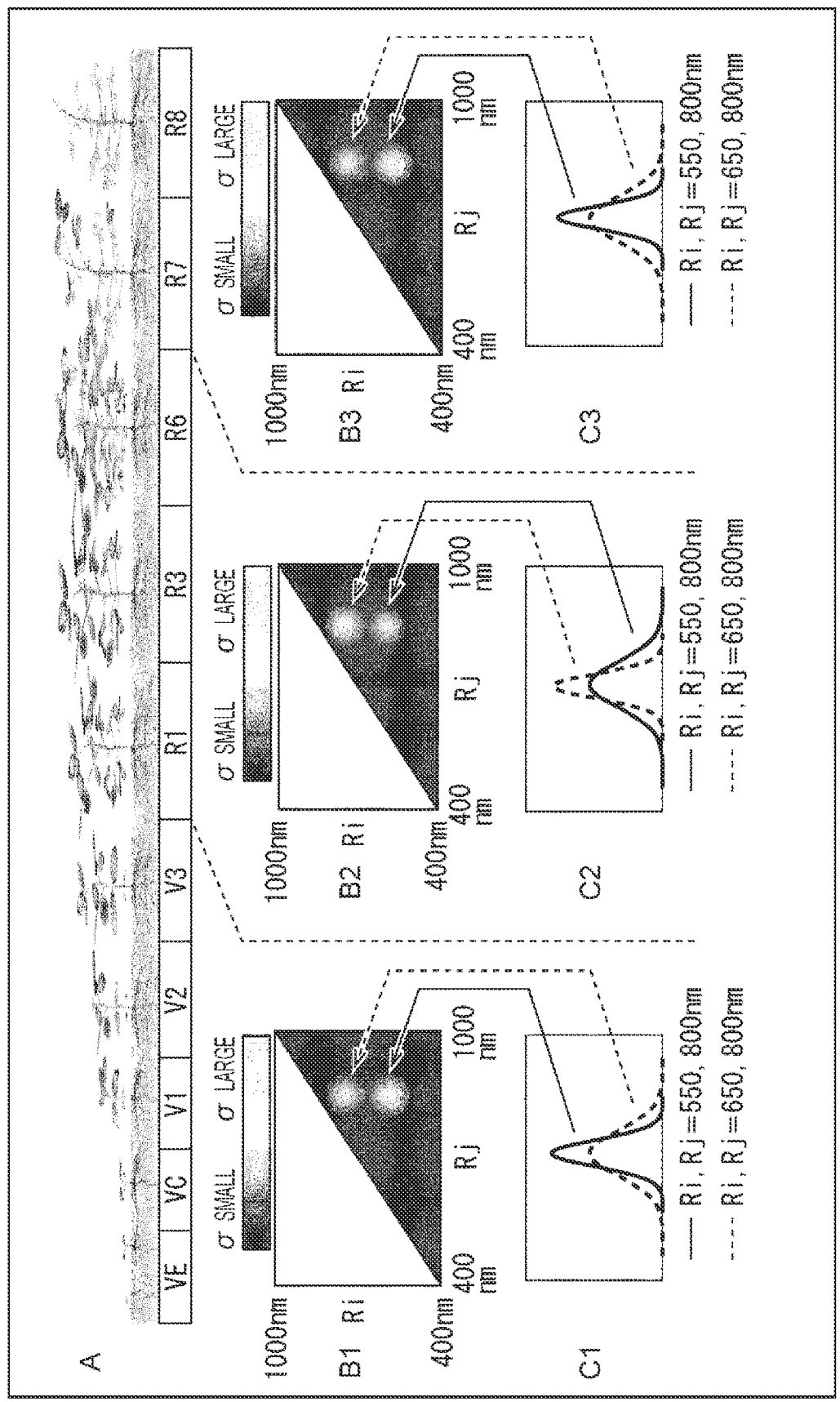
FIG. 14 is a diagram for explaining an example of an evaluation index selection method.

FIG. 14 shows an example of the state of change due to the growth of soybeans for each vegetation stage and an example of the distribution of the evaluation index.

A of FIG. 14 schematically shows the state of soybeans in each vegetation stage.

B1 to B3 of FIG. 14 are distribution charts in which the distribution of the standard deviation a of the evaluation index when the combination of the wavelength Ri and the wavelength Rj is changed is shown by the color density shown in the upper bar in a case where NDSI is used as the evaluation index. In B1 to B3 of FIG. 14, the horizontal axis indicates the wavelength Rj, and the vertical axis indicates the wavelength Ri.

B1 to B3 of FIG. 14 show that the standard deviation a is maximized in the vicinity of a combination of the wavelength Ri=550 nm (green) and the wavelength Rj=800 nm (infrared light) and a combination of the wavelength Ri=650 nm (red) and the wavelength Rj=800 nm (infrared light).

C1 to C3 of FIG. 14 show histograms of the evaluation index after normalization when NDSI is used as the evaluation index. In C1 to C3 of FIG. 14, the horizontal axis indicates a value of the evaluation index, and the vertical axis indicates a frequency. In C1 to C3 of FIG. 14, a solid line graph shows a histogram of the evaluation index in the case of the wavelength Ri=550 nm and the wavelength Rj=800 nm, and a dotted line graph shows a histogram of the evaluation index in the case of the wavelength Ri=650 nm and the wavelength Rj=800 nm.

In addition, the evaluation index in the case of the wavelength Ri=550 nm and the wavelength Rj=800 nm is called a green normalized difference vegetation index (GNDVI). In addition, the evaluation index in the case of the wavelength Ri=650 nm and the wavelength Rj=800 nm is called a normalized difference vegetation index (NDVI).

The period from a vegetation stage VE to a vegetation stage V3 is a period during which soybeans grow. In the initial stage, the soil between furrows is viewed well from above, but the area where the soil between the furrows can be viewed from above decreases as the soybeans grow. In this period, the standard deviation of the evaluation index in the case of the wavelength Ri=650 nm and the wavelength Rj=800 nm is larger than the standard deviation of the evaluation index in the case of the wavelength Ri=550 nm and the wavelength Rj=800 nm. Therefore, in this period, the evaluation index in the case of the wavelength Ri=650 nm and the wavelength Rj=800 nm is an optimal evaluation index for detecting the state or change of soybeans.

The period from a vegetation stage R1 to a vegetation stage R6 is a period after the soybeans have grown to a certain extent or more, and is a period during which the soybeans further grow with the furrows rarely viewed from above. In this period, the standard deviation of the evaluation index in the case of the wavelength Ri=550 nm and the wavelength Rj=800 nm is larger than the standard deviation of the evaluation index in the case of the wavelength Ri=650 nm and the wavelength Rj=800 nm. Therefore, in this period, the evaluation index in the case of the wavelength Ri=550 nm and the wavelength Rj=800 nm is an optimal evaluation index for detecting the state or change of soybeans.

The period from a vegetation stage R7 to a vegetation stage R8 is a period during which the color of soybeans changes from green to brown as the harvest of the soybeans approaches. In this period, the standard deviation of the evaluation index in the case of the wavelength Ri=650 nm and the wavelength Rj=800 nm becomes larger again than the standard deviation of the evaluation index in the case of the wavelength Ri=550 nm and the wavelength Rj=800 nm. Therefore, in this period, the evaluation index in the case of the wavelength Ri=650 nm and the wavelength Rj=800 nm is an optimal evaluation index for detecting the state or change of soybeans.

Therefore, by performing the above-described processing, an optimal evaluation index (optimal combination of wavelengths) is selected according to the vegetation stage of soybeans. As a result, the state or change of the soybeans is detected with higher accuracy.

In addition, in the above-described processing, for example, there is a possibility that an evaluation index based on a combination of new wavelengths will be selected. Then, by selecting an evaluation index based on a combination of new wavelengths, it is possible to accurately detect a phenomenon that was difficult to detect with a known evaluation index. In addition, for example, in a case where an unknown phenomenon (for example, occurrence of a new disease of a plant, or the like) occurs, it is possible to accurately detect the phenomenon.

Modification Example of Evaluation Value

Next, a modification example of the evaluation value used for selecting the evaluation index will be described with reference to FIGS. 15 to 18.

Second Embodiment of Evaluation Value Calculation Processing

Figure 15:
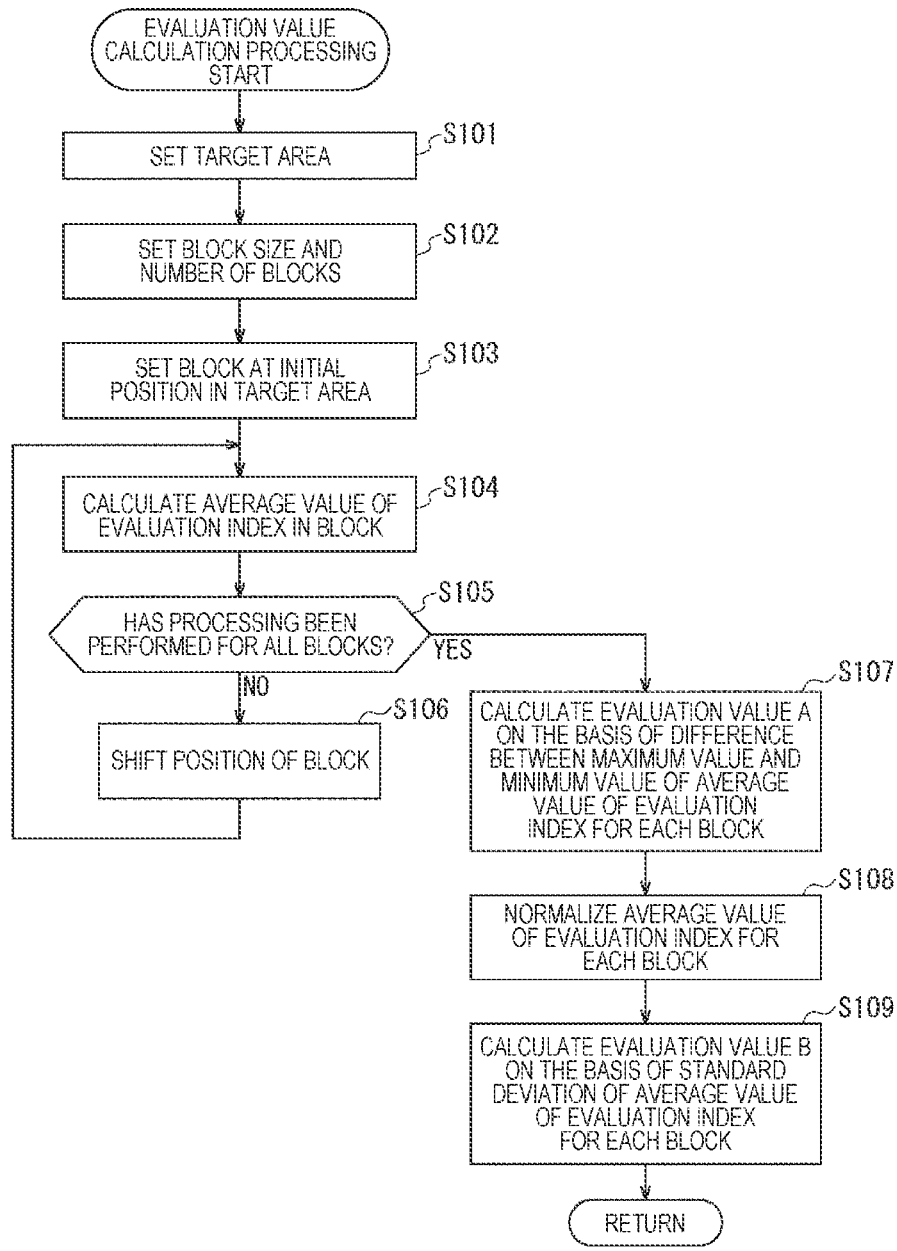
FIG. 15 is a flowchart for explaining the details of a second embodiment of the evaluation value calculation processing.

Next, a second embodiment of the evaluation value calculation processing of step S33 in FIG. 11 will be described with reference to the flowchart shown in FIG. 15.

Figure 12:
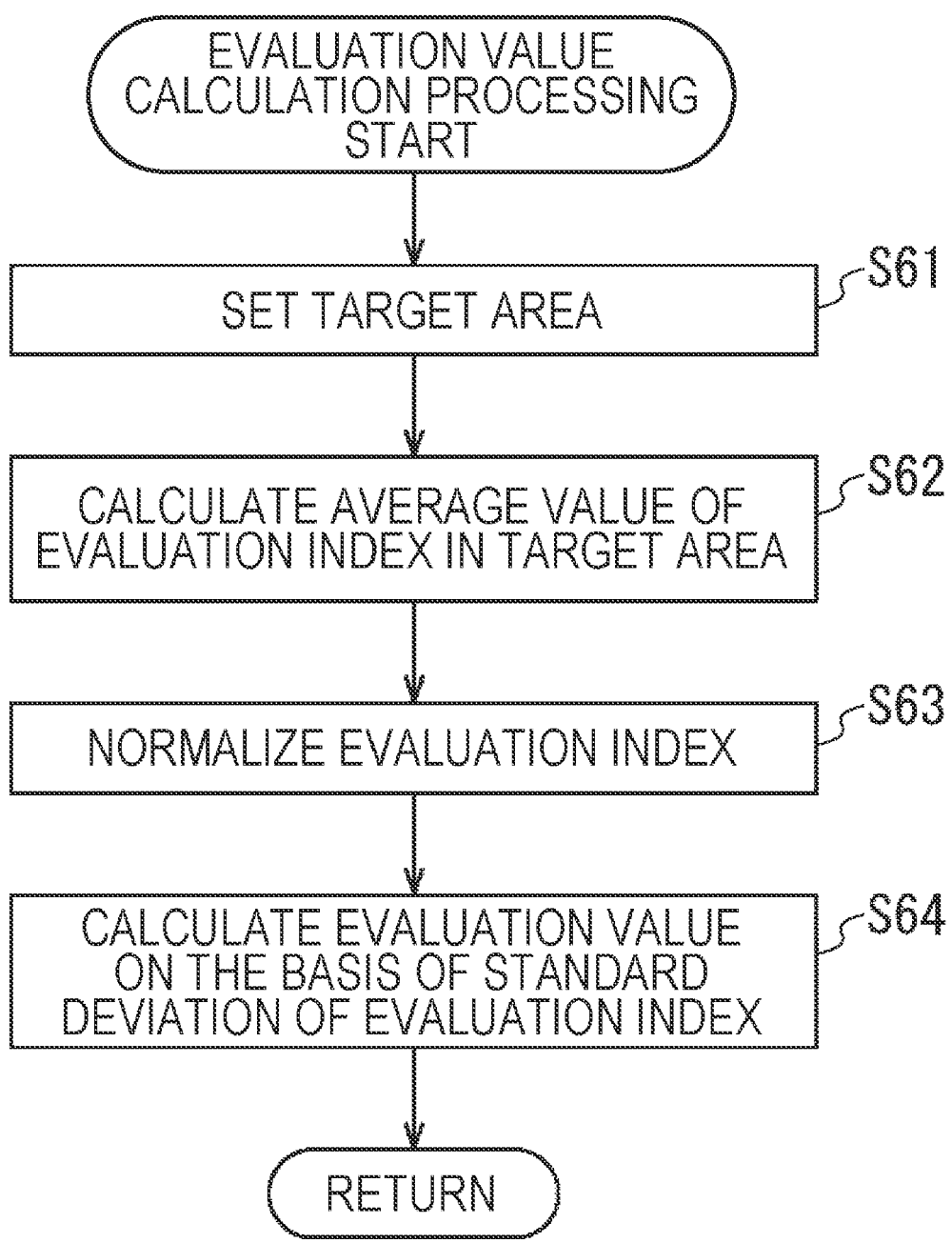
FIG. 12 is a flowchart for explaining the details of a first embodiment of evaluation value calculation processing.

In step S101, a target area is set by processing similar to the processing of step S61 in FIG. 12.

In step S102, the evaluation value calculation unit 363 sets a block size and the number of blocks.

Figure 16:
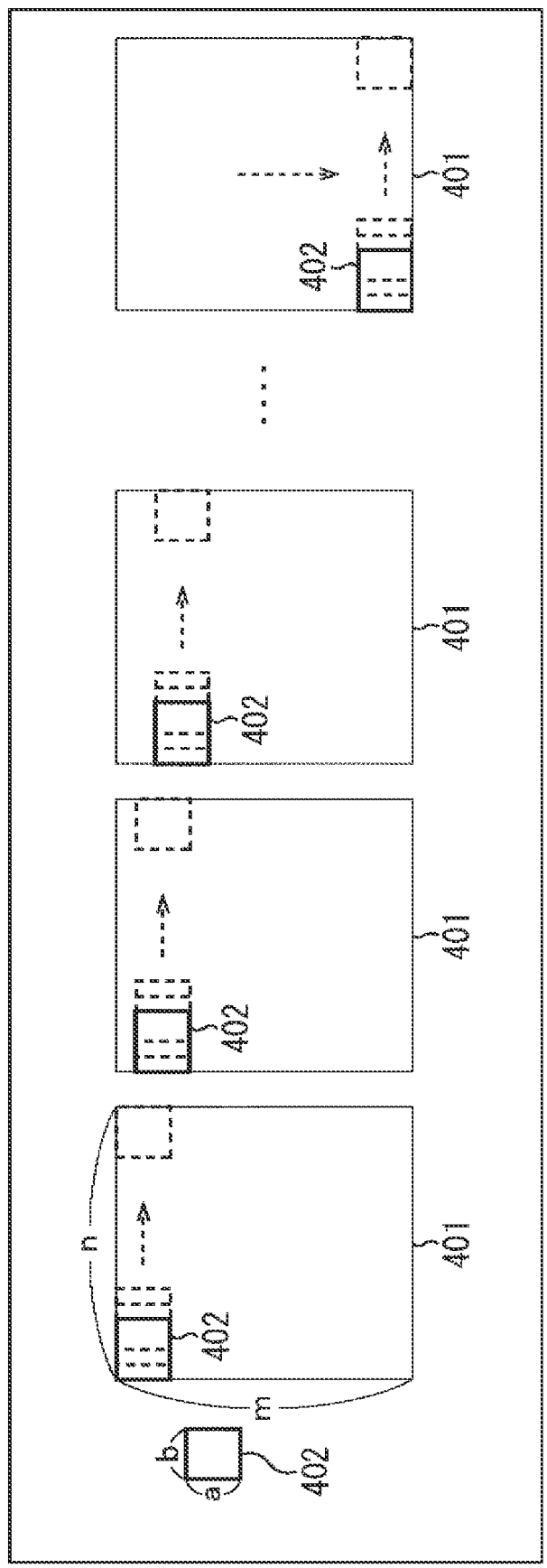
FIG. 16 is a diagram showing an example of setting a block for calculating an average value of an evaluation index.

A block is a region that includes a plurality of pixels and is a unit for calculating the average value of the evaluation index. For example, as shown in FIG. 16, for a target area 401 including m pixels vertically by n pixels horizontally, a block 402 smaller than the target area 401 is set. In addition, while shifting the block 402 by a predetermined number of pixels in the horizontal direction and the vertical direction in the target area 401, the average value of the evaluation index of the pixel in the block 402 at each position is calculated.

Then, the evaluation value calculation unit 363 sets the number of pixels a×b in the vertical direction and the horizontal direction of the block 402. In addition, the evaluation value calculation unit 363 sets the number of blocks 402 for calculating the average value of the evaluation index (the number of positions for setting the block 402). In addition, the shift amount of the block 402 (distance between the adjacent blocks 402) in the horizontal direction and the vertical direction is determined by setting the number of blocks.

For example, the block size and the number of blocks may be set by the user, or may be automatically set by the evaluation value calculation unit 363.

In addition, for example, instead of the number of blocks, the shift amount of the block 402 in the horizontal direction and the vertical direction (the number of pixels shifted in the horizontal direction and the vertical direction) may be set.

In addition, for example, instead of the shift amount, an overlap rate between the adjacent blocks 402 may be set. For example, in a case where the overlap rate is 80%, the shift amount of the block 402 is b/5 pixels in the vertical direction and a/5 pixels in the horizontal direction.

In step S103, the evaluation value calculation unit 363 sets a block at the initial position in the target area. For example, the evaluation value calculation unit 363 sets a block at the left corner of the target area.

In step S104, the evaluation value calculation unit 363 calculates an average value of the evaluation index in the block. That is, the evaluation value calculation unit 363 calculates the average value of the evaluation index by integrating the evaluation index of each pixel in the block and dividing the integrated value by the number of pixels in the block.

In step S105, the evaluation value calculation unit 363 determines whether or not the processing has been performed for all the blocks. In a case where there is a remaining block for which an average value of the evaluation index has not yet been calculated, the evaluation value calculation unit 363 determines that the processing has not yet been performed for all the blocks, and the process proceeds to step S106.

In step S106, the evaluation value calculation unit 363 shifts the position of the block. For example, in a case where the position of the current block is not the right end of the target area, the evaluation value calculation unit 363 shifts the position of the block rightward by a predetermined shift amount. On the other hand, for example, in a case where the position of the current block is the right end of the target area, the evaluation value calculation unit 363 shifts the position of the block to the left end of the target area and shifts the position of the block downward by a predetermined shift amount.

Thereafter, the process returns to step S104, and the processing of steps S104 to S106 is repeatedly executed until it is determined that the processing has been performed for all the blocks in step S105. As a result, the average value of the evaluation index for each block in the target area is calculated.

On the other hand, in step S105, in a case where there is no remaining block for which an average value of the evaluation index has not been calculated, the evaluation value calculation unit 363 determines that the processing has been performed for all the blocks, and the process proceeds to step S107.

In step S107, the evaluation value calculation unit 363 sets an evaluation value A on the basis of a difference between the maximum value and the minimum value of the average value of the evaluation index for each block.

Figure 17:
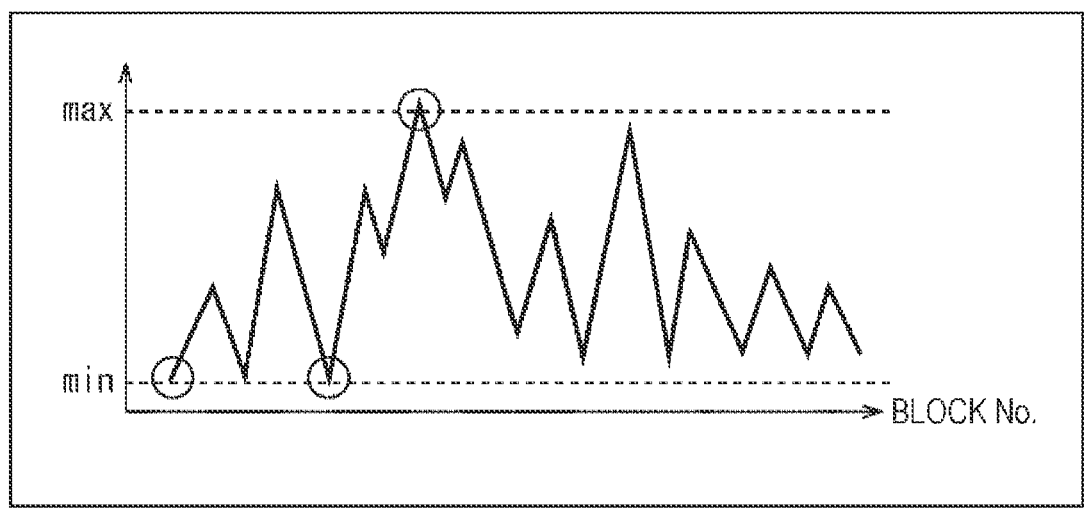
FIG. 17 is a diagram for explaining a method of calculating an evaluation value A.

FIG. 17 shows an example of the average value of the evaluation index of each block. In FIG. 17, the horizontal axis indicates the number (block No.) of each block, and the vertical axis indicates the average value of the evaluation index in the block of the block No. on the horizontal axis.

For example, the evaluation value calculation unit 363 calculates a difference between the maximum value and the minimum value of the evaluation index. Then, the evaluation value calculation unit 363 sets the calculated difference value as the evaluation value A for the evaluation index based on the current wavelength combination.

The evaluation value A indicates the variation amount of the evaluation index in the target area. Therefore, as the evaluation value A for the evaluation index becomes larger, for example, the sensitivity to information regarding the sensing area (more precisely, a region in the sensing area corresponding to the target area in the sensing image) becomes higher. For example, with an evaluation index having a larger evaluation value A, a difference or change in state in the sensing area can be expressed in more detail and quickly.

In step S108, the evaluation value calculation unit 363 normalizes the average value of the evaluation index for each block. For example, by processing similar to the processing of step S63 in FIG. 12, the evaluation value calculation unit 363 performs normalization so that the further average value of the average value of the evaluation index for each block becomes 0 in the histogram of the average value of the evaluation index for each block.

In step S109, the evaluation value calculation unit 363 sets an evaluation value B on the basis of a standard deviation of the average value of the evaluation index for each block. For example, the evaluation value calculation unit 363 calculates the standard deviation of the average value of the evaluation index for each block on the basis of the average value of the evaluation index for each block after normalization. Then, the evaluation value calculation unit 363 sets the calculated standard deviation as the evaluation value B for the evaluation index based on the current wavelength combination.

Figure 18:
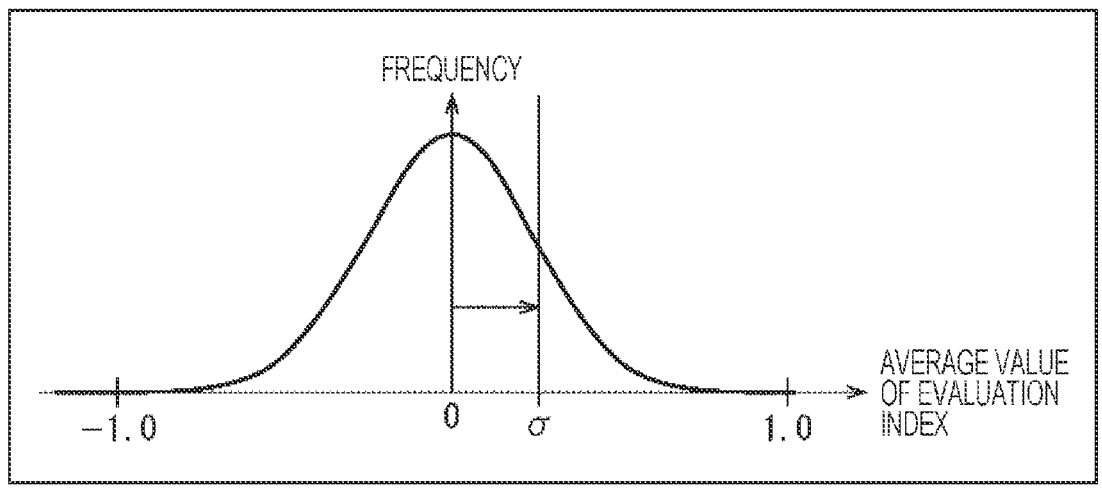
FIG. 18 is a diagram for explaining normalization processing of an average value of an evaluation index.

FIG. 18 shows an example of the histogram of the average value of the evaluation index for each block after normalization. The horizontal axis indicates the average value of the evaluation index for each block, and the vertical axis indicates a frequency. By the processing of step S109, the standard deviation a in the histogram of the average value of the evaluation index for each block after normalization is calculated and set to the evaluation value B.

This evaluation value B indicates the scattering degree of the evaluation index in the target area. Therefore, as the evaluation value B for the evaluation index becomes larger, for example, the range in which information regarding the sensing area (more precisely, a region in the sensing area corresponding to the target area in the sensing image) can be expressed becomes wider. For example, with an evaluation index having a larger evaluation value B, a difference or change in state in the sensing area can be expressed in more detail.

Thereafter, the evaluation value calculation processing is ended.

The evaluation value A and the evaluation value B for each evaluation index are calculated by executing the evaluation value calculation processing for each of a plurality of types of evaluation indices according to a combination of wavelengths.

Figure 11:
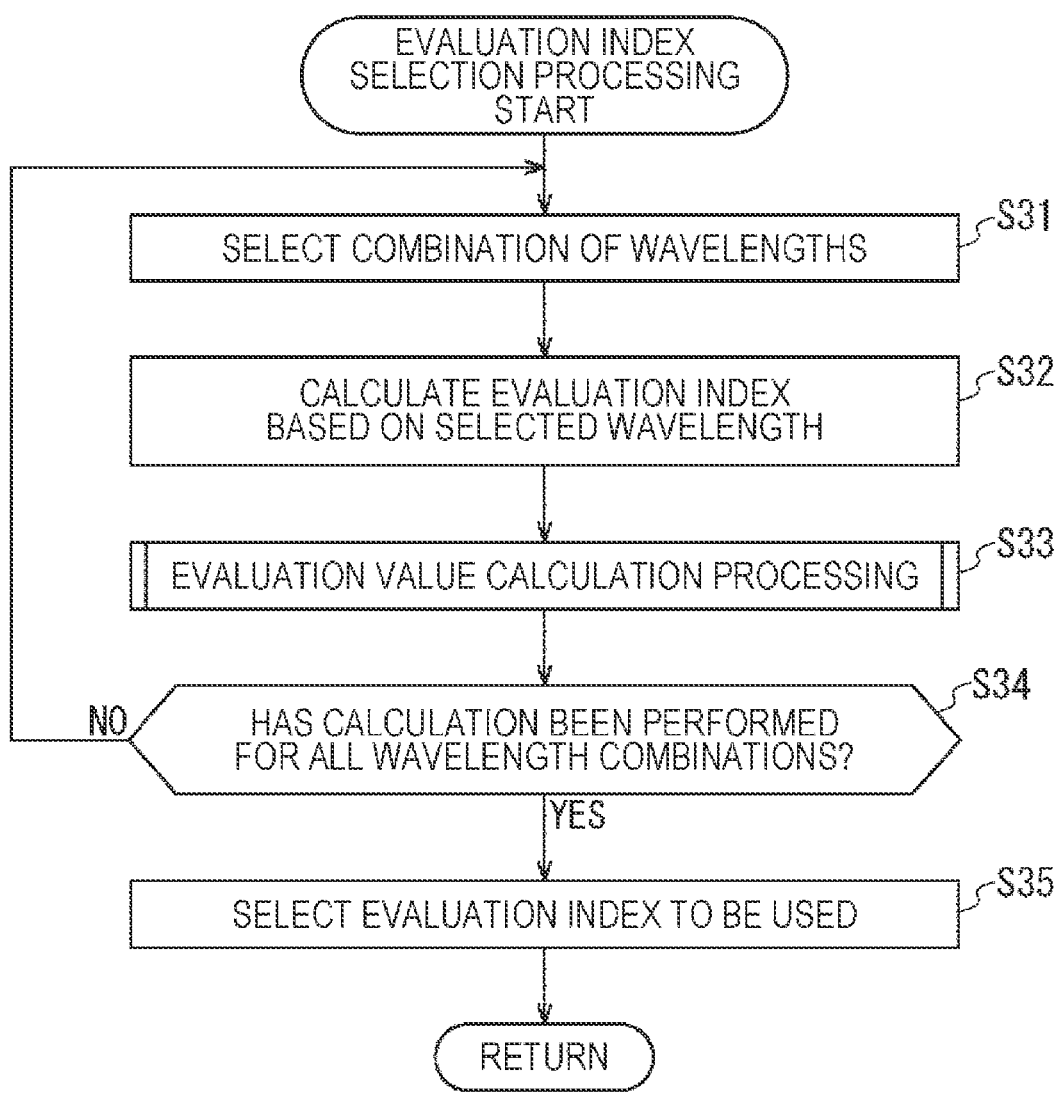
FIG. 11 is a flowchart for explaining the details of evaluation index selection processing.

Then, for example, in step S35 of FIG. 11 described above, the selection unit 364 selects an evaluation index to be used on the basis of both or one of the evaluation value A and the evaluation value B.

By selecting an evaluation index on the basis of a plurality of types of evaluation values as described above, a possibility that a more appropriate evaluation index will be selected increases.

<Processing in a Case where Sensing Area is Wide>

Next, processing in a case where the sensing area is wide will be described with reference to FIGS. 19 and 20. In this case, the sensing area is divided into a plurality of regions and imaged.

Second Embodiment of Evaluation Index Calculation Processing

First, a second embodiment of the evaluation index calculation processing executed by the information processing system 11 will be described with reference to the flowchart shown in FIG. 19.

In step S201, the remote sensing HW 101 acquires wide area sensing data. For example, the removable medium 203 storing the wide area sensing data is mounted on the drive 310 of the information processing terminal 102. The wide area sensing data includes, for example, a plurality of sensing images obtained by dividing the sensing area into a plurality of regions and performing imaging by the remote sensing HW 101 and a plurality of pieces of light source data detected at the time of imaging of each sensing image. The drive 310 reads the wide area sensing data from the removable medium 203, and supplies the read wide area sensing data to the CPU 301.

In step S202, the image processing unit 341 performs stitch processing on the sensing image. That is, the image processing unit 341 generates one sensing image (hereinafter, referred to as a stitch image) including the entire sensing area by connecting a plurality of sensing images included in the wide area sensing data to each other.

Figure 9:
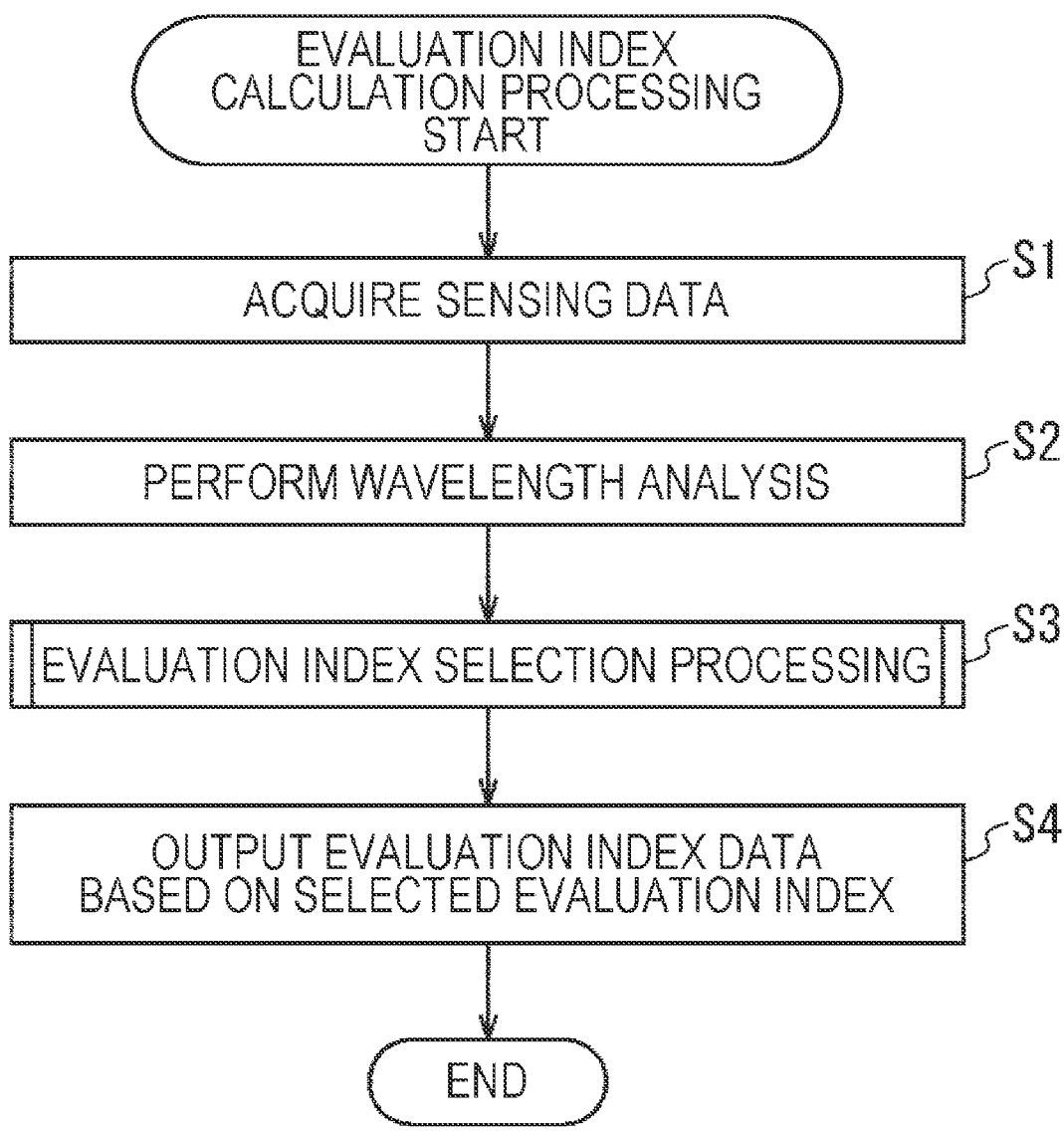
FIG. 9 is a flowchart for explaining a first embodiment of evaluation index calculation processing.
Figure 10:
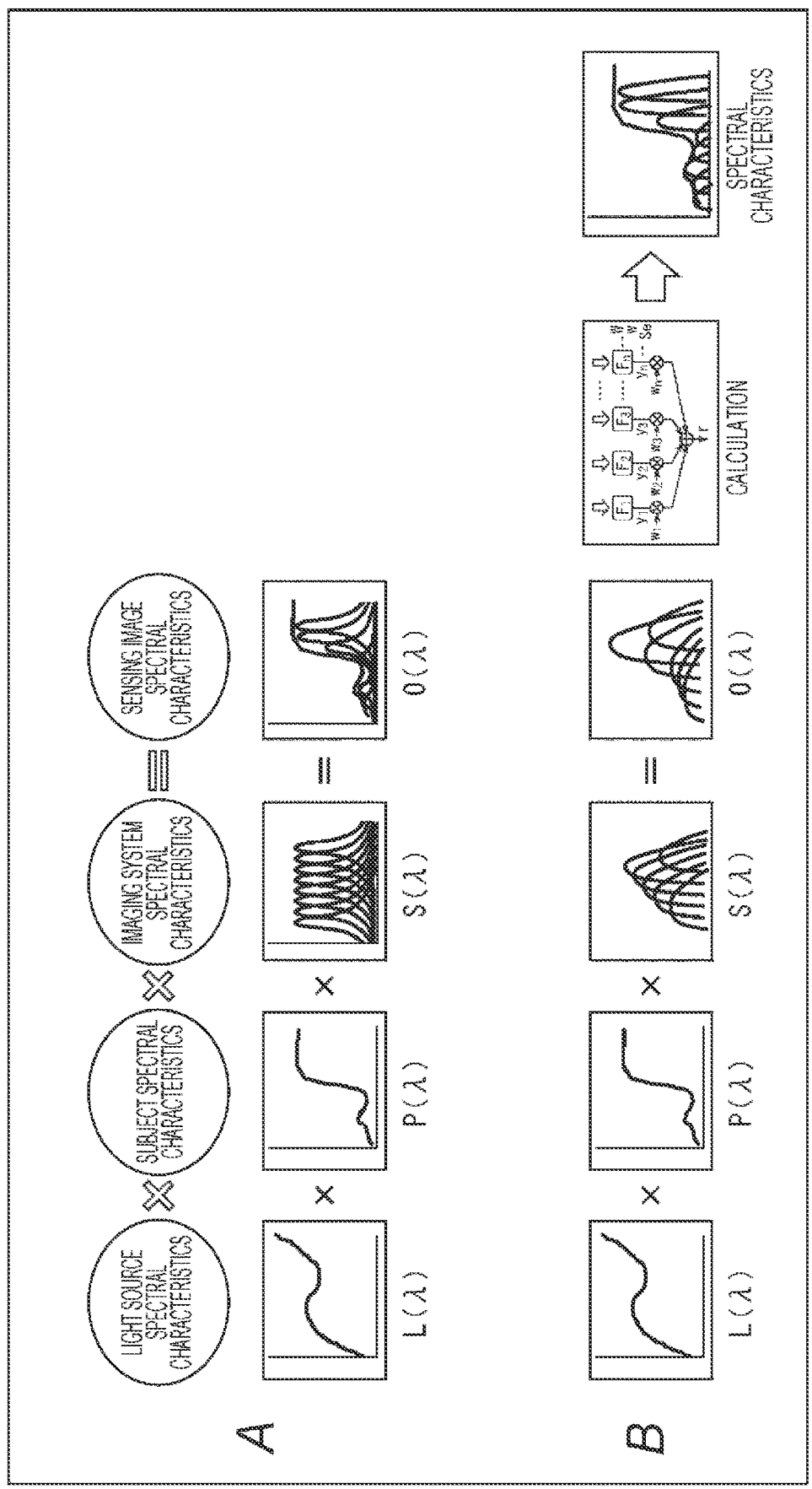
FIG. 10 is a diagram showing an example of a method of detecting the spectral characteristics of the reflectance of a subject.

Thereafter, in steps S203 to S205, processing similar to the processing of steps S2 to S4 in FIG. 9 is executed, and the evaluation index calculation processing is ended.

In this manner, an evaluation index (combination of wavelengths) suitable for the stitch image is selected, and evaluation index data based on the selected evaluation index is output. As a result, the analysis accuracy of the state, change, and the like of the wide sensing area is improved.

Third Embodiment of Evaluation Index Calculation Processing

Next, a third embodiment of the evaluation index calculation processing executed by the information processing system 11 will be described with reference to the flowchart shown in FIG. 20.

Figure 19:
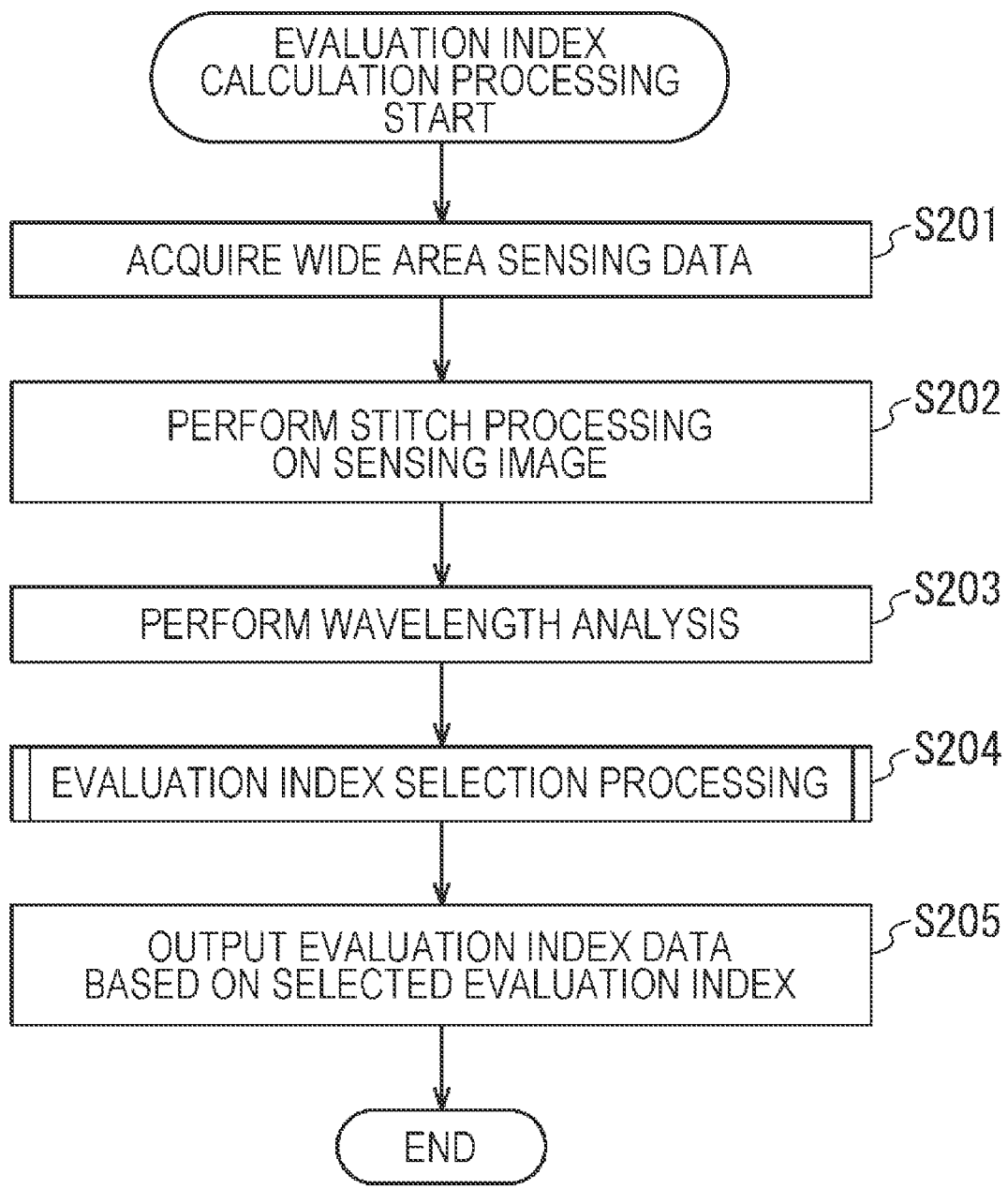
FIG. 19 is a flowchart for explaining a second embodiment of the evaluation index calculation processing.
Figure 20:
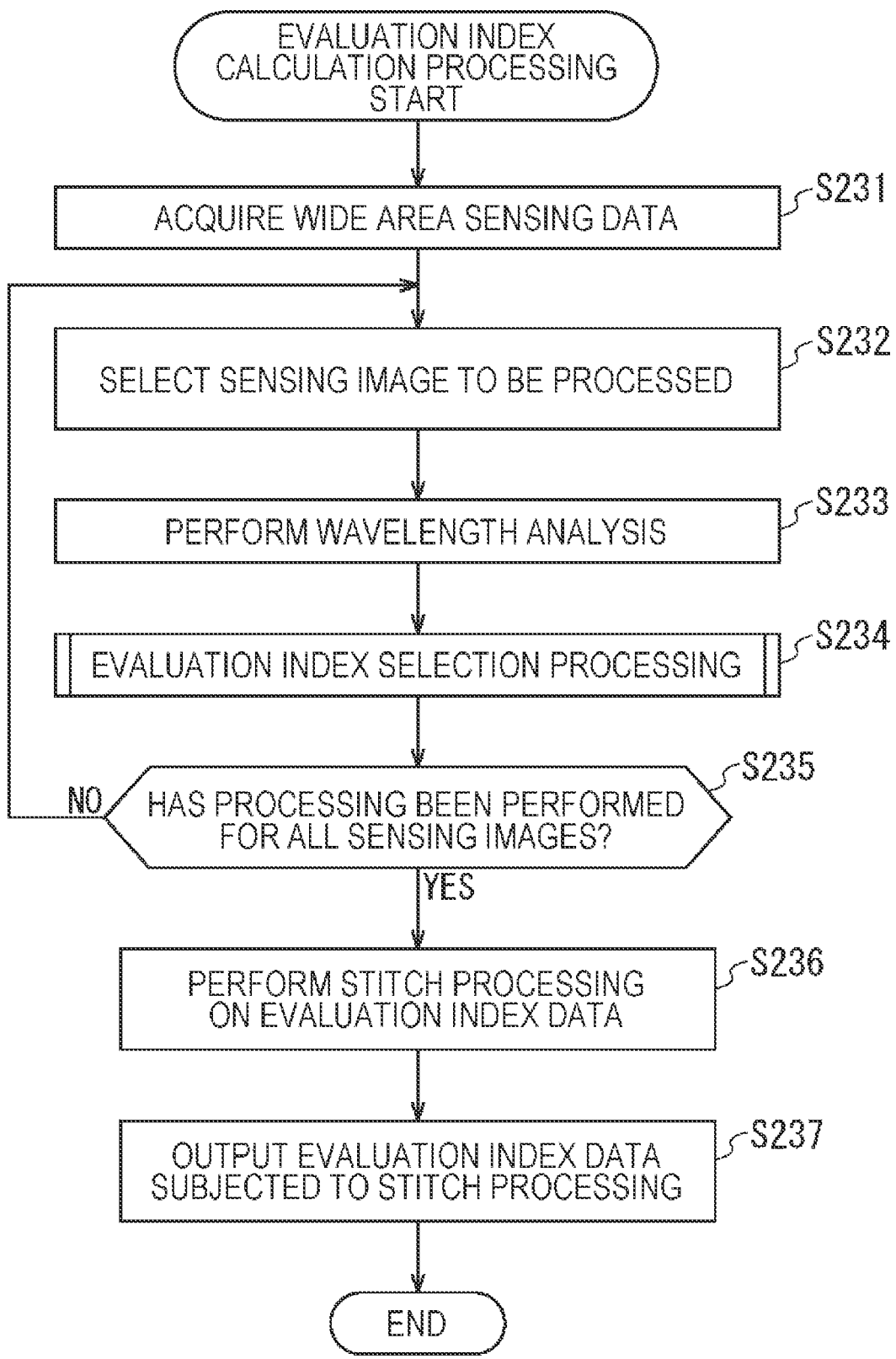
FIG. 20 is a flowchart for explaining a third embodiment of the evaluation index calculation processing.

In step S231, similarly to the processing of step S201 in FIG. 19, wide area sensing data is acquired.

In step S232, the wavelength analysis unit 361 selects a sensing image to be processed. That is, the wavelength analysis unit 361 selects one sensing image for which an evaluation index has not yet been selected among a plurality of sensing images included in the wide area sensing data.

Thereafter, in steps S233 and S234, processing similar to the processing of steps S2 and S3 in FIG. 9 is performed on the selected sensing image. As a result, an evaluation index suitable for the selected sensing image is selected.

In step S235, the wavelength analysis unit 361 determines whether or not the processing has been performed for all the sensing images. In a case where a sensing image for which an evaluation index has not been selected remains in the wide area sensing data, the wavelength analysis unit 361 determines that the processing has not yet been performed for all the sensing images, and the process proceeds to step S232.

Thereafter, the processing of steps S232 to S235 is repeatedly executed until it is determined that the processing has been performed for all the sensing images in step S235. As a result, an evaluation index suitable for each sensing image included in the wide area sensing data is individually selected.

On the other hand, in step S235, in a case where a sensing image for which an evaluation index has not been selected does not remain in the wide area sensing data, the wavelength analysis unit 361 determines that the processing has been performed for all the sensing images, and the process proceeds to step S236.

In step S236, the image processing unit 341 performs stitch processing on the evaluation index data. Specifically, the image processing unit 341 reads evaluation index data based on the evaluation index selected by the selection unit 364 from the storage unit 308 for each sensing image. As a result, evaluation index data based on the evaluation index suitable for each sensing image is read. Then, the image processing unit 341 generates evaluation index data including the entire sensing area by connecting the pieces of read evaluation index data to each other.

In step S237, the image processing unit 341 outputs the evaluation index data subjected to the stitch processing. For example, the image processing unit 341 transmits the evaluation index data subjected to the stitch processing to the storage 112 through the communication unit 309, the base station 103, and the network 111, so that the evaluation index data subjected to the stitch processing is stored in the storage 112. In addition, for example, the image processing unit 341 deletes all the pieces of evaluation index data from the storage unit 308 as necessary.

Thereafter, the evaluation index calculation processing is ended.

In this manner, an appropriate evaluation index is selected for each small region in the sensing area, and evaluation index data including the entire sensing area is generated. As a result, the analysis accuracy of the state, change, and the like of the sensing area is further improved.

<Processing in a Case of Selecting Evaluation Index on the Basis of Selection Conditions of Past Evaluation Index>

Next, processing in the case of selecting an evaluation index on the basis of conditions when an evaluation index is selected in the past without using an evaluation value will be described.

For example, in a case where the current conditions are similar to conditions when an evaluation index is selected in the past, it is possible to easily select an appropriate evaluation index by selecting the same type of evaluation index as the evaluation index selected in the past without using an evaluation value.

Fourth Embodiment of Evaluation Index Calculation Processing

Figure 21:
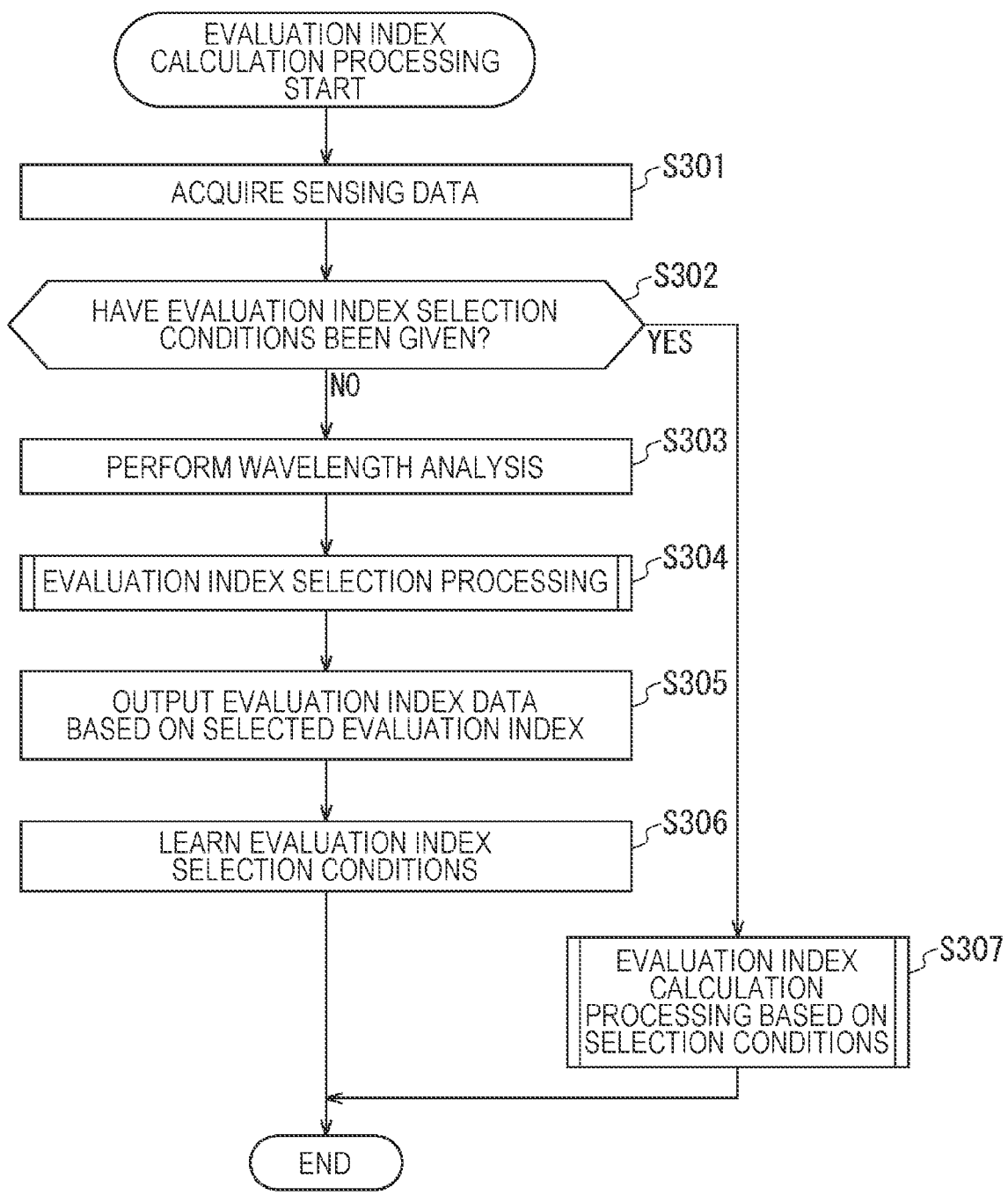
FIG. 21 is a flowchart for explaining a fourth embodiment of the evaluation index calculation processing.

Here, a fourth embodiment of the evaluation index calculation processing executed by the information processing terminal 102 will be described with reference to the flowchart shown in FIG. 21.

In step S301, similarly to the processing of step S1 in FIG. 9, sensing data is acquired.

In step S302, the selection unit 364 determines whether or not the evaluation index selection conditions have been given. In a case where it is determined that the evaluation index selection conditions have not been given, the process proceeds to step S303.

In steps S303 to S305, processing similar to the processing of steps S2 to S4 in FIG. 9 described above is executed. In this manner, similarly to the processing described above, an evaluation index suitable for the sensing image is selected on the basis of the evaluation value, and evaluation index data based on the selected evaluation index is output.

In step S306, the learning unit 344 learns the evaluation index selection conditions. For example, the learning unit 344 acquires data indicating the conditions when the evaluation index is selected in the processing of step S304.

The conditions acquired herein are not particularly limited as long as the conditions are conditions regarding the selection of the evaluation index. For example, one or more of temporal conditions such as season, date and time, and time zone, environmental conditions such as weather, temperature, humidity, and altitude, conditions regarding the sensing area such as country name, region name, and area type (for example, agricultural land, urban area, factory, desert, and the like), conditions regarding the analysis target such as plant type and vegetation stage, and conditions regarding the analysis content such as detection of vegetation activity, disease detection, and pest damage detection are acquired.

In addition, these conditions may be input by the user through the input unit 306 or may be acquired by the learning unit 344 itself, for example.

Then, the learning unit 344 learns the evaluation index selection conditions selected this time on the basis of the type of the selected evaluation index and the acquired data. Then, the learning unit 344 updates an evaluation index database stored in the storage unit 308 on the basis of the learning result.

The evaluation index database is, for example, a database in which the type of evaluation index and the evaluation index selection conditions are associated with each other. For example, the selection unit 364 can select an evaluation index on the basis of the selection conditions by searching for an evaluation index, which matches the given selection conditions, from the evaluation index database.

Thereafter, the evaluation index calculation processing is ended.

On the other hand, for example, in a case where the user performs an operation for inputting the evaluation index selection conditions through the input unit 306, the output unit 307 displays an input screen of the evaluation index selection conditions under the control of the output control unit 343. In response to this, the user inputs the evaluation index selection conditions through the input unit 306.

Then, in a case where data indicating the input selection conditions is supplied from the input unit 306, the selection unit 364 determines that evaluation index selection conditions have been given in step S302, and the process proceeds to step S307.

In step S307, the information processing terminal 102 executes evaluation index calculation processing based on the selection conditions, and then ends the evaluation index calculation processing.

Figure 22:
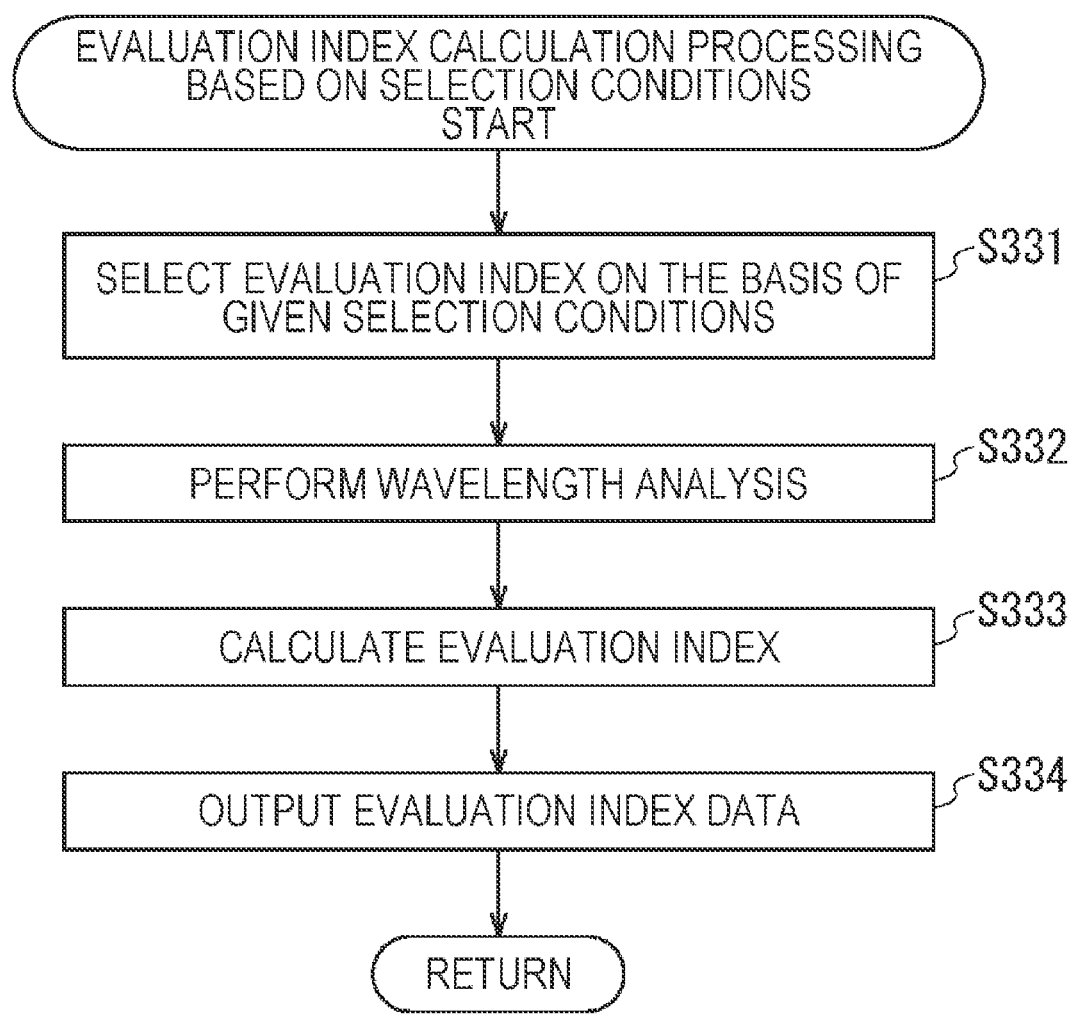
FIG. 22 is a flowchart for explaining the details of evaluation index calculation processing based on selection conditions.

Here, the details of the evaluation index calculation processing based on the selection conditions will be described with reference to the flowchart shown in FIG. 22.

In step S331, the selection unit 364 selects an evaluation index on the basis of the given selection conditions. For example, the selection unit 364 selects an evaluation index matching the given selection conditions or corresponding to selection conditions having the highest similarity among the evaluation indices registered in the evaluation index database stored in the storage unit 308.

For example, as in the example of FIG. 14 described above, in the case of observing the growth process of soybeans, soybeans as a plant type and a vegetation stage are given as selection conditions. Therefore, in a case where the vegetation stage given as the selection conditions is any one of the vegetation stage VE to the vegetation stage V3, the vegetation stage R7, and the vegetation stage R8, an evaluation index of the wavelength Ri=650 nm and the wavelength Rj=800 nm is selected. In a case where the vegetation stage given as the selection conditions is any one of the vegetation stage R1 to the vegetation stage R6, an evaluation index of the wavelength Ri=550 nm and the wavelength Rj=800 nm is selected.

In addition, it is possible to select a more appropriate evaluation index by giving the analysis content, such as detection of vegetation activity, disease detection, and pest damage detection, as the selection conditions, for example.

In addition, a plurality of types of evaluation indices may be selected. In addition, for example, a plurality of types of selected evaluation index candidates may be presented to the user for the user's selection.

In step S332, the wavelength analysis unit 361 performs wavelength analysis. That is, the wavelength analysis unit 361 performs wavelength analysis of the reflectance of the subject by processing similar to the processing of step S2 in FIG. 9, thereby detecting the reflectance of the subject with respect to the light having a wavelength necessary for the selected evaluation index for each pixel of the sensing image. The wavelength analysis unit 361 supplies data indicating the detection result to the evaluation index calculation unit 362.

In step S333, the evaluation index calculation unit 362 calculates an evaluation index. That is, on the basis of the reflectance of the subject detected by the wavelength analysis unit 361, the evaluation index calculation unit 362 calculates the evaluation index selected by the selection unit 364 for each pixel of the sensing image. In addition, the evaluation index calculation unit 362 generates evaluation index data in which the evaluation indices of the respective pixels of the sensing image are arranged in the arrangement order of the pixels.

In step S334, the evaluation index data is output by processing similar to the processing of step S4 in FIG. 9.

Thereafter, the evaluation index calculation processing based on the selection conditions is ended.

As described above, in a case where the selection conditions are given, the evaluation index is selected on the basis of the given selection conditions without using the evaluation value, and the evaluation index data based on the selected evaluation index is generated. As a result, the load of the evaluation index calculation processing is reduced, and the processing time is shortened.

In addition, by updating the evaluation index database on the basis of the learning result, a more appropriate evaluation index is selected for the given selection conditions. For example, in the case of analyzing the sensing area every year, the evaluation index database is updated every year on the basis of the selected evaluation index and the selected selection conditions. This increases a possibility that a more appropriate evaluation index will be selected for the analysis of the sensing area as time passes.

2. Second Embodiment

Next, a second embodiment of the present technology will be described with reference to FIGS. 23 to 27.

<Configuration Example of Information Processing System 501>

Figure 23:
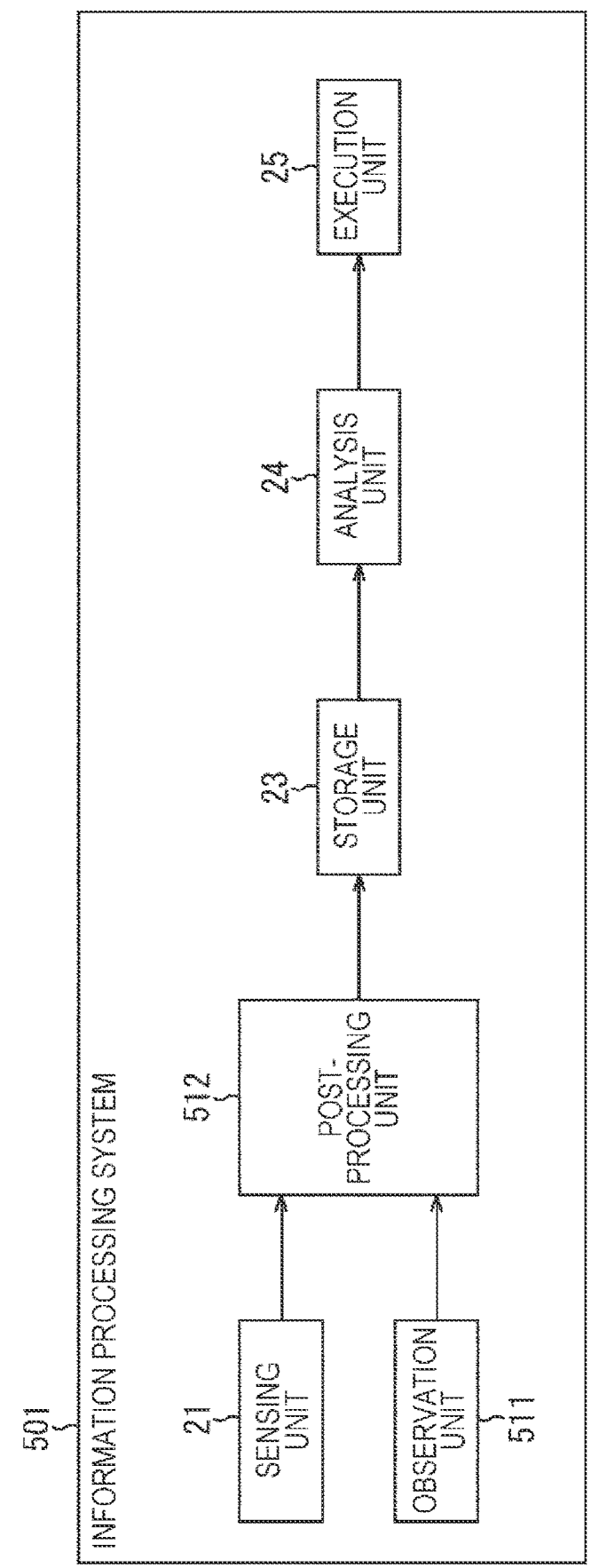
FIG. 23 is a block diagram showing a second embodiment of the information processing system to which the present technology is applied.

FIG. 23 shows a second embodiment of the information processing system to which the present technology is applied. In addition, in the diagram, portions corresponding to those in the information processing system 11 shown in FIG. 1 are denoted by the same reference numerals, and the description thereof will be appropriately omitted.

An information processing system 501 shown in FIG. 23 is different from the information processing system 11 in that an observation unit 511 is added and a post-processing unit 512 is added instead of the post-processing unit 22.

The observation unit 511 acquires various kinds of observation data regarding the sensing area other than sensing data (sensing image and light source data). The observation unit 511 supplies the acquired observation data to the post-processing unit 512.

The post-processing unit 512 has a function of learning the correlation between the evaluation index and the observation data in addition to the function of the post-processing unit 22 of the information processing system 11.

Figure 24:
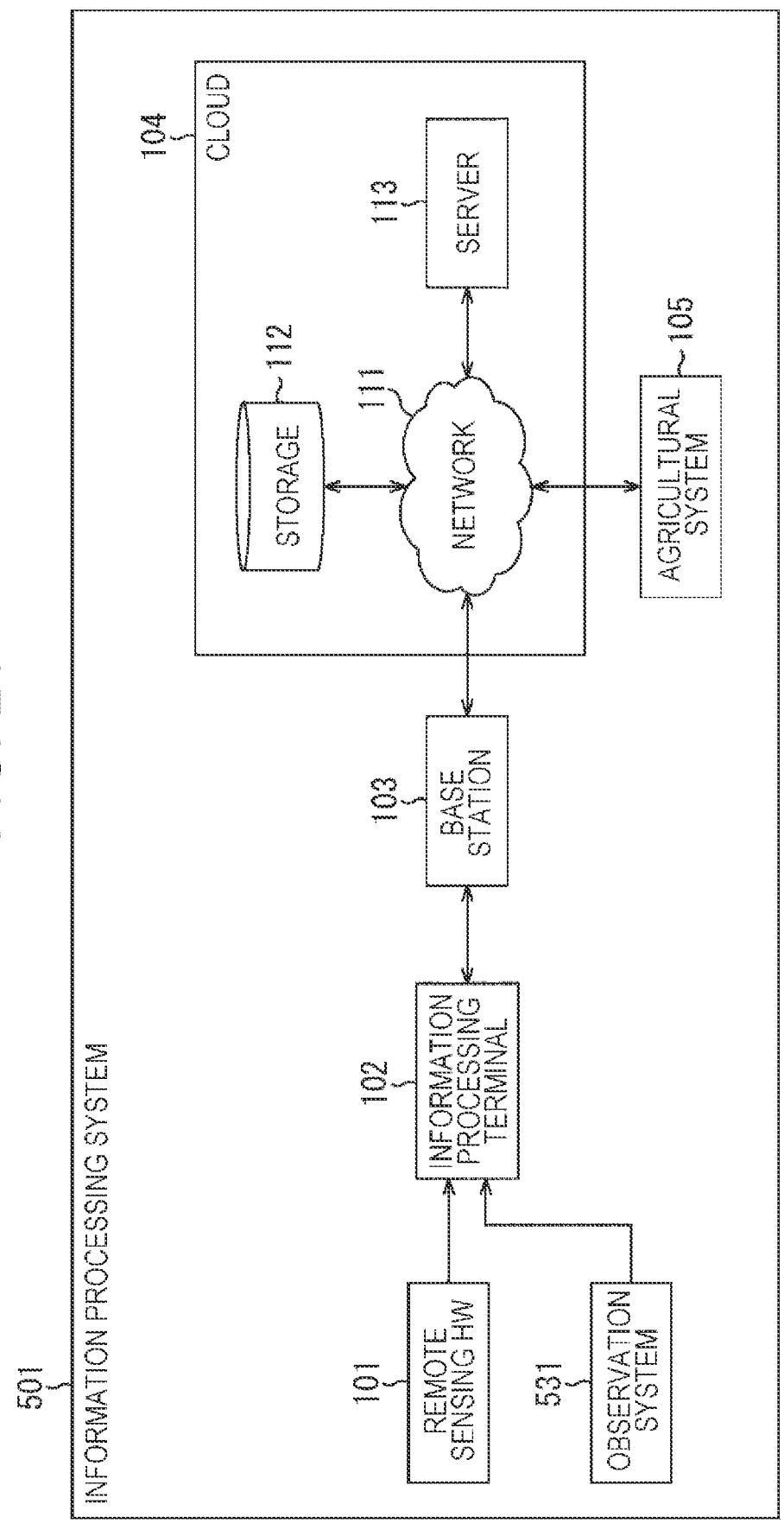
FIG. 24 is a block diagram showing a specific configuration example of the information processing system shown in FIG. 23.

FIG. 24 shows a more specific configuration example of the information processing system 501 in FIG. 23. In addition, in the diagram, portions corresponding to those in the information processing system 11 shown in FIG. 2 are denoted by the same reference numerals, and the description thereof will be appropriately omitted.

The information processing system 501 shown in FIG. 24 is different from the information processing system 11 shown in FIG. 2 in that an observation system 531 is added.

The observation system 531 includes an apparatus for acquiring various kinds of observation data regarding the sensing area other than the sensing data, or the like, and has a function of the observation unit 511 shown in FIG. 23. For example, the observation unit 511 includes a vegetation inspection machine that detects data indicating the state of plants, such as a stomatal conductance measuring machine and a gas exchange type photosynthesis measuring machine. The observation system 531 supplies the acquired observation data to the information processing terminal 102.

The information processing terminal 102 has a function of the post-processing unit 512 shown in FIG. 23.

<Configuration Example of Information Processing Unit 561>

Figure 25:
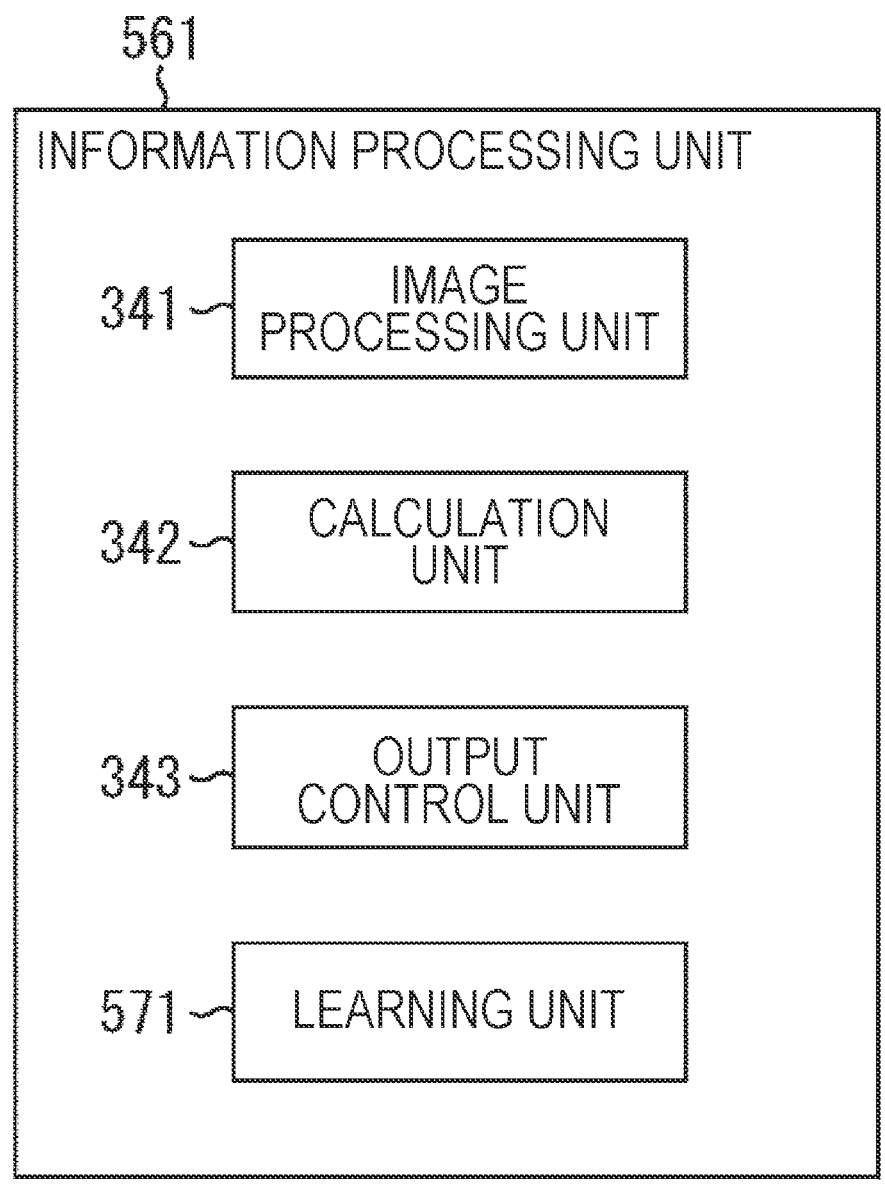
FIG. 25 is a block diagram showing a second embodiment of the information processing unit.

FIG. 25 shows a configuration example of the information processing unit 561 realized by executing a predetermined control program by the CPU 301 of the information processing terminal 102.

In addition, in the diagram, portions corresponding to those in the information processing unit 331 shown in FIG. 7 are denoted by the same reference numerals, and the description thereof will be appropriately omitted.

The information processing unit 561 is different from the information processing unit 331 in that a learning unit 571 is provided instead of the learning unit 344.

The learning unit 571 has a function of learning the correlation between the evaluation index and the observation data in addition to the function of the learning unit 344.

Evaluation Index Calculation Processing

Figure 26:
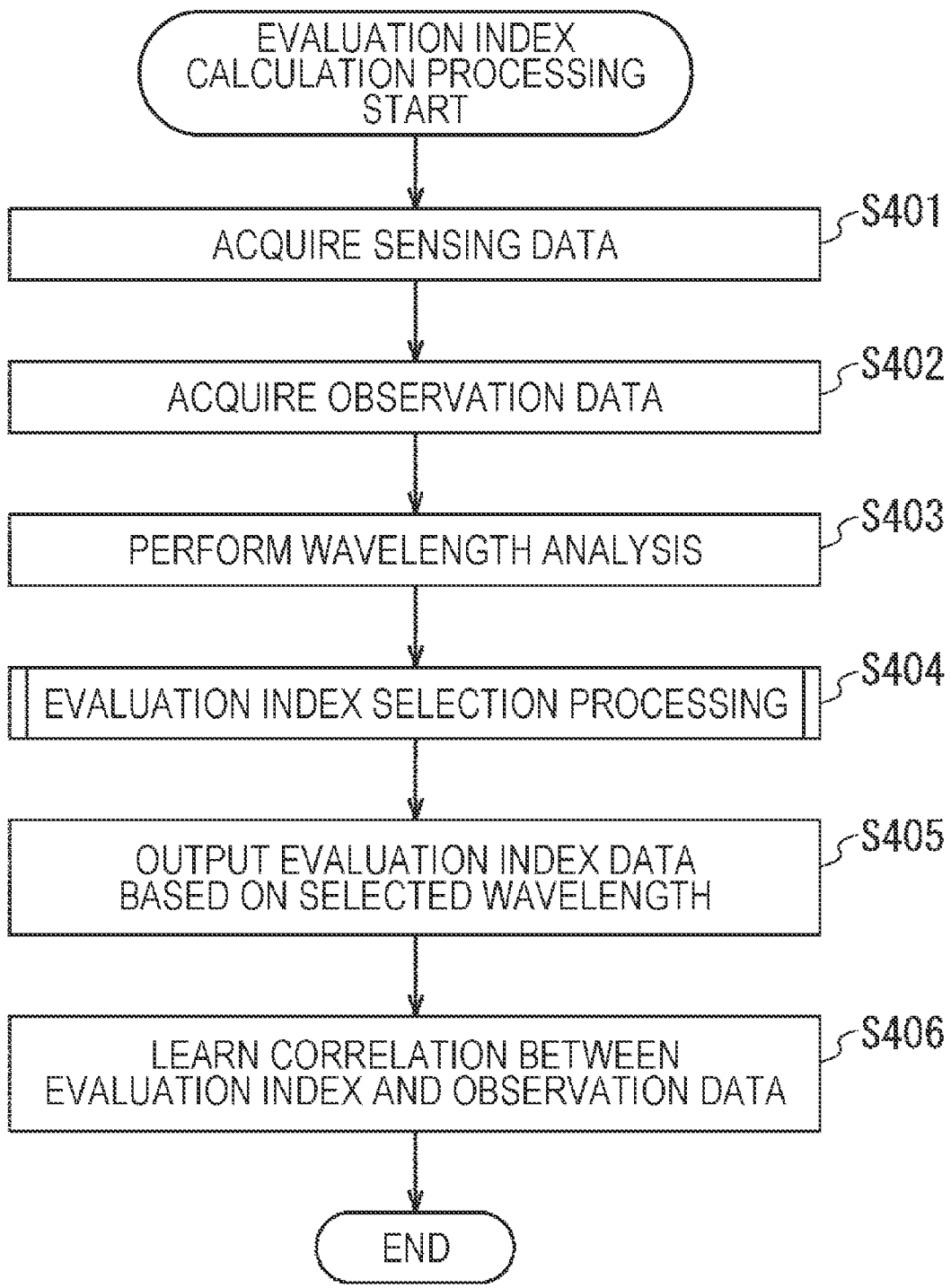
FIG. 26 is a flowchart for explaining a fifth embodiment of the evaluation index calculation processing.

Next, a fifth embodiment of evaluation index calculation processing executed by the information processing terminal 102 will be described with reference to the flowchart shown in FIG. 26.

In step S401, similarly to the processing of step S1 in FIG. 9, sensing data is acquired.

In step S402, the information processing terminal 102 acquires observation data.

For example, the observation system 531 acquires observation data in a region where the features of the evaluation index data noticeably appear (hereinafter, referred to as a "feature region") and a region in the sensing area corresponding to the surrounding region. The feature region is, for example, a region where the tendency of the evaluation index is significantly different from the other regions, or the like.

The type of observation data is set according to the sensing area, analysis content, and the like. For example, in a case where the sensing area is an agricultural land and analysis of the ecology of plants in the agricultural land is performed, data regarding the ecology of plants is included in the observation data. For example, stomatal conductance, a gas exchange amount, and the like are included in the observation data.

In steps S403 to S405, processing similar to the processing of steps S2 to S4 in FIG. 9 is executed. As a result, an evaluation index suitable for the sensing image is selected, and evaluation index data based on the selected evaluation index is output.

In step S406, the learning unit 571 learns the correlation between the evaluation index and the observation data. For example, the learning unit 571 calculates a coefficient of correlation with the evaluation index for each of a plurality of types of pieces of observation data. In addition, any method can be used as a method of calculating the correlation coefficient.

Then, the learning unit 571 extracts observation data highly correlated with the evaluation index on the basis of the calculated correlation coefficient.

Then, for example, on the basis of the extracted observation data, a phenomenon occurring in the feature region is specified. As a result, the correlation between the evaluation index and a phenomenon expressed by the observation data highly correlated with the evaluation index is further learned. Specification of a phenomenon may be performed by the learning unit 571 or by the user, for example.

The specified phenomenon is a phenomenon highly correlated with the evaluation index. That is, the specified phenomenon is a phenomenon that can be detected with high accuracy on the basis of the evaluation index.

Figure 27:
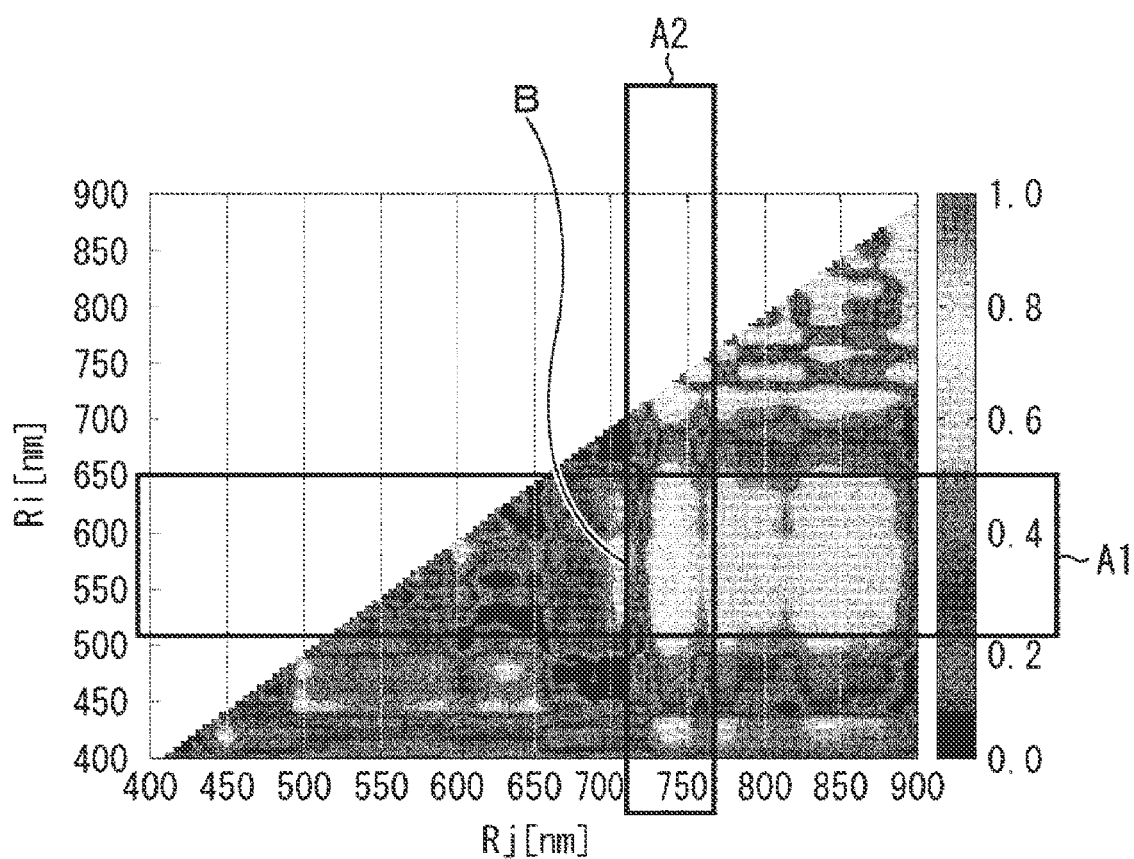
FIG. 27 is a diagram showing an example of the correlation between an evaluation index and observation data.

FIG. 27 is a graph showing an example of the correlation between the evaluation index and the observation data. The horizontal axis indicates the wavelength Rj used for the evaluation index, and the vertical axis indicates the wavelength Ri used for the evaluation index. In addition, in a triangular region in the graph, a correlation coefficient between the observation data and the evaluation index based on the combination of the wavelength Ri and the wavelength Rj is shown on the basis of the color density of a bar on the right side of the graph.

This example shows that the correlation between the evaluation index and the observation data is strong in a case where the wavelength Ri is within a range indicated by the frame A1 and the wavelength Rj is within a range indicated by the frame A2. Therefore, by using the evaluation index based on the combination of the wavelength Ri and the wavelength Rj within a range B where the frame A1 and the frame A2 cross each other, it is possible to accurately detect a phenomenon expressed by the observation data.

As described above, for example, it is possible to develop a new evaluation index. For example, in a case where an evaluation index based on the combination of wavelengths not present in the past is selected, it is possible to specify the meaning of the new evaluation index. That is, since it is possible to specify a phenomenon that can be detected by a new evaluation index, a new evaluation index can be used for detection of the phenomenon.

3. Modification Example

Hereinafter, modification examples of the above embodiments of the present technology will be described.

Modification Example Relevant to Evaluation Index

The evaluation index applicable to the present technology is not limited to the NDSI described above, and other evaluation indices can be used.

For example, an evaluation index based on one wavelength component of a sensing image may be adopted, and an evaluation index to be used may be selected from a plurality of types of evaluation indices having different wavelength components.

For example, an evaluation index based on a combination of three or more wavelength components of a sensing image may be adopted, and an evaluation index to be used may be selected from a plurality of types of evaluation indices having different combinations of wavelength components.

For example, an evaluation index to be used may be selected from a plurality of types of evaluation indices having different numbers of wavelength components user for calculation.

For example, an evaluation index to be used may be selected from a plurality of types of evaluation indices which are based on the same wavelength components of the sensing image but whose calculation methods and the like are different.

For example, an evaluation index to be used may be selected from a plurality of types of evaluation indices whose wavelength components, calculation methods, and the like are different.

In addition, the evaluation value used for the selection of the evaluation index is not limited to the examples described above, and other statistical values of the evaluation index may be used.

For example, instead of the standard deviation of the evaluation index, a variance may be used.

For example, a statistical value indicating the magnitude of a change in the evaluation index other than the standard deviation or the variation amount of the evaluation index described above may be used.

In addition, it is possible to use not only the statistical value indicating the magnitude of a change in the evaluation index in a spatial direction (in the sensing image) but also a statistical value indicating the magnitude of a change in the evaluation index in a temporal direction. For example, the evaluation value may be calculated on the basis of the variance, standard deviation, variation amount, or the like in the time-series distribution of the evaluation index. In addition, for example, the evaluation value may be calculated on the basis of a statistical value indicating the magnitude of a change in the evaluation index in both the spatial direction and the temporal direction.

In addition, instead of using the statistical value as it is as an evaluation value, for example, the statistical value may be changed to the evaluation value by a predetermined calculation expression.

In addition, the present technology can also be applied to a case where the evaluation index is calculated not for each pixel of the sensing image but for each block including a plurality of pixels, for example.

Modification Example Relevant to System Configuration

The above-described configuration examples of the information processing system 11 and the information processing system 501 are just examples, and can be changed as necessary.

For example, it is possible to change the sharing of the functions of the respective units of the information processing system 11 and the information processing system 501.

For example, as shown in FIG. 28, the sharing of the sensing unit 21, the post-processing unit 22, and the storage unit 23 of the information processing system 11 may be changed.

A of FIG. 28 shows an example in a case where the remote sensing HW 101 has a function of the sensing unit 21, the information processing terminal 102 has a function of the post-processing unit 22, and the cloud 104 has a function of the storage unit 23, as described above.

On the other hand, for example, as shown in B of FIG. 28, the remote sensing HW 101 may have the functions of the sensing unit 21 and the post-processing unit 22, and the information processing terminal 102 may have the function of the storage unit 23.

In addition, for example, as shown in C of FIG. 28, the remote sensing HW 101 may have the function of the sensing unit 21, and the information processing terminal 102 may have the functions of the post-processing unit 22 and the storage unit 23.

In addition, for example, as shown in D of FIG. 28, the remote sensing HW 101 may have the function of the sensing unit 21, and the cloud 104 may have the functions of the post-processing unit 22 and the storage unit 23.

In addition, for example, the information processing terminal 102 may have all or some of the functions of the analysis unit 24 of the information processing system 11 or the information processing system 501. In addition, for example, the information processing terminal 102 may have all or some of the functions of the execution unit 25 of the information processing system 11 or the information processing system 501. In addition, for example, the sensing unit 21 may have all or some of the functions of the observation unit 511 of the information processing system 501.

In addition, for example, the control unit 212 of the sensor box 201 and the control unit 225 of the camera 202 in the remote sensing HW 101 may be used in common.

In addition, for example, a sensor capable of detecting the spectral characteristics of the light source of ambient light more accurately may be provided in the remote sensing HW 101.

Other Modification Examples

In the above description, an example is shown in which the spectral characteristics of the subject are detected on the basis of the spectral characteristics of the sensing image and the evaluation index is calculated on the basis of the spectral characteristics of the subject. However, for example, the evaluation index may be calculated on the basis of the spectral characteristics of the sensing image instead of using the spectral characteristics of the subject. In this case, for example, it is possible to omit the sensor box 201 of the remote sensing HW 101.

In addition, in the above description, an example is shown in which the evaluation index is calculated on the basis of the sensing image obtained by imaging the imaging data obtained by imaging the subject (sensing area). However, the evaluation index may be calculated on the basis of imaging data (for example, spectral data) before imaging. That is, in the present technology, the evaluation index may be calculated on the basis of imaging data either before imaging or after imaging. Here, the imaging is processing for arranging the data of each pixel or performing various kinds of image processing so that the imaging data can be displayed as an image, for example.

4. Others

<Program Providing Method and the Like>

The series of processes described above can be executed by hardware or can be executed by software. In the case of executing the series of processes by software, a program of the software is installed on a computer (for example, the CPU 301 of the information processing terminal 102). Here, examples of the computer include a computer built into dedicated hardware and a general-purpose personal computer or the like capable of executing various functions by installing various programs.

For example, in the information processing terminal 102, the CPU 301 loads a program recorded in the storage unit 308 to the RAM 303 through the input and output interface 305 and the bus 304 and executes the program, so that the series of processes are performed, for example.

In addition, the program executed by the information processing terminal 102 (CPU 301) can be provided in a state in which the program is recorded on the removable medium 203 as a package medium, for example. In addition, the program can be provided through a wired or wireless transmission medium, such as a local area network, the Internet, and digital satellite broadcasting.

In the information processing terminal 102, the program can be installed on the storage unit 308 through the input and output interface 305 by mounting the removable medium 203 on the drive 310. In addition, the program can be received by the communication unit 309 through a wired or wireless transmission medium and installed on the storage unit 308. In addition, the program can be installed on the ROM 302 or the storage unit 308 in advance.

In addition, the program executed by the computer may be a program by which processes are performed in time series according to the order described in this specification, or may be a program by which processes are performed in parallel or at necessary timings, such as when a call is made.

In addition, in this specification, the system means a group of a plurality of constituent elements (apparatuses, modules (components), and the like), and it does not matter whether all constituent elements are in the same housing or not. Therefore, a plurality of apparatuses, which are housed in separate housings and are connected to each other through a network, and one apparatus, in which a plurality of modules are housed in one housing, are both systems.

In addition, embodiments of the present technology are not limited to the embodiments described above, and various modifications can be made without departing from the gist of the present technology.

For example, the present technology can adopt a configuration of cloud computing in which one function is shared by a plurality of apparatuses through a network so as to be cooperatively processed.

In addition, each step described in the above-described flowchart can be executed by one apparatus or can be shared by a plurality of apparatuses.

In addition, in a case where a plurality of processes are included in one step, the plurality of processes included in the one step can be executed by one apparatus or can be shared by a plurality of apparatuses.

Combination Example of Configuration

The present technology can also adopt the following configuration.

(1) An information processing apparatus including:
an evaluation index calculation unit that calculates a plurality of types of evaluation indices on the basis of imaging data obtained by imaging a subject;
an evaluation value calculation unit that calculates an evaluation value based on a statistical value of each of the evaluation indices for each of the evaluation indices; and a selection unit that selects the evaluation index on the basis of the evaluation value.
(2) The information processing apparatus described in (1), in which the evaluation index calculation unit calculates each of the evaluation indices for each different wavelength component of the imaging data.
(3) The information processing apparatus described in (2), in which the evaluation index calculation unit calculates each of the evaluation indices for each combination of two or more wavelength components of the imaging data.
(4) The information processing apparatus described in (3), in which the evaluation index is a normalized difference spectral index (NDSI).
(5) The information processing apparatus described in any one of (1) to (4),
in which the evaluation index calculation unit calculates each of the evaluation indices for each pixel of the imaging data or for each block including a plurality of pixels.
(6) The information processing apparatus described in (5), in which the statistical value indicates a magnitude of a change in the evaluation index in all or a part of the imaging data.
(7) The information processing apparatus described in (6), in which the statistical value is a variance or a standard deviation of the evaluation index in all or a part of the imaging data.
(8) The information processing apparatus described in (6) or (7),
in which the statistical value is a variation amount of the evaluation index in all or a part of the imaging data.
(9) The information processing apparatus described in any one of (1) to (8), further including:
a wavelength analysis unit that extracts a plurality of wavelength components from the imaging data.
(10) The information processing apparatus described in any one of (1) to (9), further including:
an image processing unit that generates a second image by connecting a plurality of first images corresponding to a plurality of pieces of first imaging data to each other,
in which the evaluation index calculation unit calculates the plurality of types of evaluation indices on the basis of the second image.
(11) The information processing apparatus described in any one of (1) to (9),
in which the evaluation index calculation unit calculates the plurality of types of evaluation indices for a plurality of first images corresponding to a plurality of pieces of first imaging data, respectively,
the selection unit individually selects the evaluation index for each of the first images, and
an image processing unit that connects a plurality of second images based on the evaluation index selected for each of the first images to each other is further provided.
(12) The information processing apparatus described in any one of (1) to (11), further including:
an analysis unit that analyzes the subject on the basis of the selected evaluation index.
(13) The information processing apparatus described in any one of (1) to (12),
in which the selection unit selects the evaluation index for new imaging data on the basis of conditions when the evaluation index is selected in a past, and
the evaluation index calculation unit calculates the selected evaluation index on the basis of the new imaging data.
(14) The information processing apparatus described in (13), further including:
a learning unit that learns selection conditions, which are used for selection of the evaluation index, on the basis of the conditions when the evaluation index is selected in the past,
in which the selection unit selects the evaluation index for the new imaging data on the basis of the selection conditions.
(15) The information processing apparatus described in any one of (1) to (12), further including:
a learning unit that learns a correlation between the evaluation index and observation data different from the imaging data.
(16) The information processing apparatus described in (15), in which the learning unit further learns a correlation between the evaluation index and a phenomenon expressed by the observation data.
(17) An information processing method including:
calculating a plurality of types of evaluation indices on the basis of imaging data obtained by imaging a subject by an information processing apparatus;
calculating an evaluation value based on a statistical value of each of the evaluation indices for each of the evaluation indices by the information processing apparatus; and
selecting the evaluation index on the basis of the evaluation value by the information processing apparatus.
(18) A program causing a computer to execute processes of:
calculating a plurality of types of evaluation indices on the basis of imaging data obtained by imaging a subject;
calculating an evaluation value based on a statistical value of each of the evaluation indices for each of the evaluation indices; and
selecting the evaluation index on the basis of the evaluation value.
(A1) An information processing apparatus, comprising:
an evaluation index unit that determines a plurality of evaluation indices on a basis of imaging data obtained by imaging a subject, wherein the evaluation indices are respectively based upon different wavelength component combinations of the imaging data;

an evaluation value unit that determines an evaluation value based on a statistical value of each of the evaluation indices, for each of the evaluation indices; and a selection unit that determines a selected evaluation index from the evaluation indices on a basis of the evaluation value.

(A2) The information processing apparatus according to (A1), wherein the evaluation index unit calculates each of the evaluation indices using different wavelength components of the imaging data.

(A3) The information processing apparatus according to (A2), wherein the evaluation index unit calculates each of the evaluation indices using the different wavelength component combinations of the imaging data, wherein each wavelength component combination comprises two or more wavelength components of the imaging data.

(A4) The information processing apparatus according to (A3), wherein the evaluation index is a normalized difference spectral index (NDSI).

(A5) The information processing apparatus according to (A1), wherein the evaluation index unit determines each of the evaluation indices corresponding to at least one of: individual pixels of the imaging data or respective blocks of pixels of the imaging data.

(A6) The information processing apparatus according to (A5), wherein the statistical value indicates a magnitude of a change in each respective evaluation index in all or a part of the imaging data.

(A7) The information processing apparatus according to (A6), wherein the statistical value is a variance or a standard deviation of each respective evaluation index in all or a part of the imaging data.

(A8) The information processing apparatus according to (A6), wherein the statistical value is a variation amount of each respective evaluation index in all or a part of the imaging data.

(A9) The information processing apparatus according to (A1), further comprising:

a wavelength analysis unit that extracts a plurality of wavelength components from the imaging data to provide the different wavelength component combinations.

(A10) The information processing apparatus according to (A1), further comprising:

an image processing unit that generates a second image by connecting together a plurality of first images corresponding to a plurality of pieces of first imaging data, wherein the evaluation index unit determines the plurality of evaluation indices on a basis of the second image.

(A11) The information processing apparatus according to (A1), wherein the evaluation index unit determines the plurality of evaluation indices for a plurality of first images corresponding to a plurality of pieces of first imaging data, respectively, the selection unit individually determines the selected evaluation index for each of the first images, and wherein the information processing unit further comprises an image processing unit that connects together a plurality of second images based on the evaluation index selected for each of the first images.

(A12) The information processing apparatus according to (A1), further comprising:

an analysis unit that analyzes the subject on a basis of the selected evaluation index.

(A13) The information processing apparatus according to (A1), wherein the selection unit determines the selected evaluation index for new imaging data on a basis of conditions corresponding to a prior selection of the evaluation index, and the evaluation index unit determines the selected evaluation index on a basis of the new imaging data.

(A14) The information processing apparatus according to (A13), further comprising:

a learning unit that learns selection conditions, which are used for selection of the evaluation index, on a basis of the conditions corresponding to at least one prior selection of the evaluation index, wherein the selection unit determines the selected evaluation index for the new imaging data on a basis of the selection conditions.

(A15) The information processing apparatus according to (A1), further comprising:

a learning unit that learns a correlation between the evaluation index and observation data different from the imaging data.

(A16) The information processing apparatus according to (A15), wherein the learning unit further learns a correlation between the evaluation index and a phenomenon expressed by the observation data.

(A17) The information processing apparatus according to (A1), wherein the selection unit determines the selected evaluation index on a basis of at least one of a vegetation stage or a plant type of the subject.

(A18) An information processing method, comprising:

determining a plurality of evaluation indices on a basis of imaging data obtained by imaging a subject, wherein the evaluation indices are respectively based upon different wavelength component combinations of the imaging data;

determining an evaluation value based on a statistical value of each of the evaluation indices, for each of the evaluation indices; and determining a selected evaluation index from the evaluation indices on a basis of the evaluation value by the information processing apparatus.

(A19) A non-transitory computer readable medium storing program code executable by a processor to perform operations comprising:

determining a plurality of evaluation indices on a basis of imaging data obtained by imaging a subject, wherein the evaluation indices are respectively based upon different wavelength component combinations of the imaging data;

determining an evaluation value based on a statistical value of each of the evaluation indices, for each of the evaluation indices; and determining a selected evaluation index from the evaluation indices on a basis of the evaluation value.

(A20) An apparatus comprising:

a processor; and a memory, the memory storing program code executable by the processor to perform operations comprising:

determining a plurality of evaluation indices on a basis of imaging data obtained by imaging a subject, wherein the evaluation indices are respectively based upon different wavelength component combinations of the imaging data;

determining an evaluation value based on a statistical value of each of the evaluation indices, for each of the evaluation indices; and determining a selected evaluation index from the evaluation indices on a basis of the evaluation value.

In addition, the effects described in this specification are merely examples and are not limited, and there may be other effects.

REFERENCE SIGNS LIST

11 Information processing system
21 Sensing unit
22 Post-processing unit
23 Storage unit
24 Analysis unit
25 Execution unit
101 Remote sensing HW
102 Information processing terminal
104 Cloud computing
105 Agricultural system
112 Storage
113 Server
201 Sensor box
202 Camera
203 Removable medium
211 Illuminance sensor
212 Control unit
222 Imaging unit
223 Signal processing unit
225 Control unit
241 Filter
242 Image sensor
261 Drone
301 CPU
331 Information processing unit
341 Image processing unit
342 Calculation unit
343 Output control unit
344 Learning unit
361 Wavelength analysis unit
362 Evaluation index calculation unit
363 Evaluation value calculation unit
364 Selection unit
401 Selection area
402 Block
501 Information processing system
511 Observation unit
512 Post-processing unit
531 Observation system
561 Information processing unit
571 Learning unit

The invention claimed is:

1. An information processing method, comprising:
determining a plurality of evaluation indices on a basis of imaging data obtained by imaging a subject, wherein the evaluation indices are respectively based upon different wavelength component combinations of the imaging data;
determining an evaluation value based on a statistical value of each of the evaluation indices, for each of the evaluation indices; and
determining a selected evaluation index from the evaluation indices on a basis of the evaluation value by the information processing apparatus.

2. A non-transitory computer readable medium storing program code executable by a processor to perform operations comprising:
determining a plurality of evaluation indices on a basis of imaging data obtained by imaging a subject, wherein the evaluation indices are respectively based upon different wavelength component combinations of the imaging data;
determining an evaluation value based on a statistical value of each of the evaluation indices, for each of the evaluation indices; and
determining a selected evaluation index from the evaluation indices on a basis of the evaluation value.

3. The non-transitory computer readable medium according to claim 2, wherein the operations further comprise:
calculating each of the evaluation indices using different wavelength components of the imaging data.

4. The non-transitory computer readable medium according to claim 3, wherein the operations further comprise:
calculating each of the evaluation indices using the different wavelength component combinations of the imaging data, wherein each wavelength component combination comprises two or more wavelength components of the imaging data.

5. The non-transitory computer readable medium according to claim 4, wherein the evaluation index is a normalized difference spectral index (NDSI).

6. The non-transitory computer readable medium according to claim 2, wherein the operations further comprise:
determining each of the evaluation indices corresponding to at least one of individual pixels of the imaging data or respective blocks of pixels of the imaging data.

7. The non-transitory computer readable medium according to claim 6, wherein the statistical value indicates a magnitude of a change in each respective evaluation index in all or a part of the imaging data.

8. The non-transitory computer readable medium according to claim 7, wherein the statistical value is a variance or a standard deviation of each respective evaluation index in all or a part of the imaging data.

9. The non-transitory computer readable medium according to claim 7, wherein the statistical value is a variation amount of each respective evaluation index in all or a part of the imaging data.

10. An apparatus comprising:
a processor; and
a memory, the memory storing program code executable by the processor to perform operations comprising:
determining a plurality of evaluation indices on a basis of imaging data obtained by imaging a subject, wherein the evaluation indices are respectively based upon different wavelength component combinations of the imaging data;
determining an evaluation value based on a statistical value of each of the evaluation indices, for each of the evaluation indices; and
determining a selected evaluation index from the evaluation indices on a basis of the evaluation value.

11. The apparatus according to claim 10, wherein the operations further comprise:
calculating each of the evaluation indices using different wavelength components of the imaging data.

12. The apparatus according to claim 11, wherein the operations further comprise:
calculating each of the evaluation indices using the different wavelength component combinations of the imaging data, wherein each wavelength component combination comprises two or more wavelength components of the imaging data.

13. The apparatus according to claim 12, wherein the evaluation index is a normalized difference spectral index (NDSI).

14. The apparatus according to claim 10, wherein the operations further comprise:
  determining each of the evaluation indices corresponding to at least one of individual pixels of the imaging data or respective blocks of pixels of the imaging data.

15. The apparatus according to claim 14, wherein the statistical value indicates a magnitude of a change in each respective evaluation index in all or a part of the imaging data.

16. The apparatus according to claim 15, wherein the statistical value is a variance or a standard deviation of each respective evaluation index in all or a part of the imaging data.

17. The apparatus according to claim 15, wherein the statistical value is a variation amount of each respective evaluation index in all or a part of the imaging data.

18. The apparatus according to claim 10, wherein the operations further comprise:
  extracting a plurality of wavelength components from the imaging data to provide the different wavelength component combinations.

19. The apparatus according to claim 10, wherein the operations further comprise:
  generating a second image by connecting together a plurality of first images corresponding to a plurality of pieces of first imaging data; and
  determining the plurality of evaluation indices on a basis of the second image.

20. The apparatus according to claim 10, wherein the operations further comprise:
  determining the plurality of evaluation indices for a plurality of first images corresponding to a plurality of pieces of first imaging data, respectively;
  individually determining the selected evaluation index for each of the first images; and
  connecting together a plurality of second images based on the evaluation index selected for each of the first images.

21. The apparatus according to claim 10, wherein the operations further comprise:
  analyzing the subject on a basis of the selected evaluation index.

22. The apparatus according to claim 10, wherein the operations further comprise:
  determining the selected evaluation index for new imaging data on a basis of conditions corresponding to a prior selection of the evaluation index; and
  determining the selected evaluation index on a basis of the new imaging data.

23. The apparatus according to claim 22, wherein the operations further comprise:
  learning selection conditions, which are used for selection of the evaluation index, on a basis of the conditions corresponding to at least one prior selection of the evaluation index; and
  determining the selected evaluation index for the new imaging data on a basis of the selection conditions.

24. The apparatus according to claim 10, wherein the operations further comprise:
  learning a correlation between the evaluation index and observation data different from the imaging data.

25. The information processing apparatus according to claim 24, wherein the operations further comprise:
  learning a correlation between the evaluation index and a phenomenon expressed by the observation data.

26. The information processing apparatus according to claim 10, wherein the operations further comprise:
  determining the selected evaluation index on a basis of at least one of a vegetation stage or a plant type of the subject.

* * * * *